(12) United States Patent
Olson

(10) Patent No.: US 8,412,314 B2
(45) Date of Patent: Apr. 2, 2013

(54) LOCATION AND DISPLAYING AN ISCHEMIC REGION FOR ECG DIAGNOSTICS

(76) Inventor: Charles Olson, Huntington Station, NY (US)

( * ) Notice: Subject to any disclaimer, the term of this patent is extended or adjusted under 35 U.S.C. 154(b) by 434 days.

(21) Appl. No.: 12/710,943

(22) Filed: Feb. 23, 2010

(65) Prior Publication Data

US 2010/0249622 A1    Sep. 30, 2010

Related U.S. Application Data

(63) Continuation-in-part of application No. 11/411,365, filed on Apr. 25, 2006, now Pat. No. 7,751,874.

(60) Provisional application No. 60/674,789, filed on Apr. 25, 2005, provisional application No. 61/169,047, filed on Apr. 14, 2009.

(51) Int. Cl.
*A61B 5/0402* (2006.01)

(52) U.S. Cl. .......................... 600/512; 600/509; 600/523

(58) Field of Classification Search .................. 600/509, 600/512, 523
See application file for complete search history.

(56) References Cited

U.S. PATENT DOCUMENTS

| | | |
|---|---|---|
| 3,186,403 A | 6/1965 | Bassett |
| 3,333,580 A | 8/1967 | Fawcett |
| 3,710,174 A | 1/1973 | Cerniglia, Jr. |
| 3,816,849 A | 6/1974 | Kinoshita et al. |
| 4,136,690 A | 1/1979 | Anderson et al. |
| 4,175,337 A | 11/1979 | Benjo |
| 4,292,977 A | 10/1981 | Krause et al. |
| 4,478,223 A | 10/1984 | Allor |
| 4,528,988 A | 7/1985 | Wong |
| 4,537,202 A | 8/1985 | Mancini et al. |
| 4,587,976 A | 5/1986 | Schmid et al. |
| 4,697,597 A | 10/1987 | Sanz et al. |
| 4,700,712 A | 10/1987 | Schmid |
| 4,850,370 A | 7/1989 | Dower |

(Continued)

FOREIGN PATENT DOCUMENTS

SU    1526645    12/1989

OTHER PUBLICATIONS

Te-Chuan Chou et al., "Clinical Vectorcardiography": Foreword (2 pages); "Section I—Chapter 1—The Vector Concept" Fig. 1.1; Fig. 1.2 (2 pages); Fig. 5.3—Mean values of various measurements of QRS and Tloops—Grune & Stratton, Inc., New York and London, 1967.

(Continued)

*Primary Examiner* — Christopher D Koharski
*Assistant Examiner* — Natasha Patel
(74) *Attorney, Agent, or Firm* — John F. Vodopia

(57) ABSTRACT

A method for locating an ischemic region in the heart of a subject includes establishing three dimensional coordinates axes with respect to the torso of the subject as a reference; establishing as a reference a multi-dimensional representation of the heart defining at least three dimensional coordinate axes of the heart, the multi-dimensional representation defining at least the base of the heart and a middle section of the heart to thereby prescribe a surface of the heart on the reference multi-dimensional representation of the heart; and orienting the three dimensional coordinate axes of the heart from an initial position offset with respect to the three dimensional coordinates with respect to the torso of the subject to an imaginary position wherein at least one axis of the heart is parallel to or coincident with at least one of the three dimensional coordinate axes with respect to the torso of the subject. Corresponding displays are disclosed also.

17 Claims, 30 Drawing Sheets

U.S. PATENT DOCUMENTS

| | | | |
|---|---|---|---|
| 4,898,181 | A | 2/1990 | Kessler |
| 4,922,920 | A | 5/1990 | Thie et al. |
| 4,949,725 | A | 8/1990 | Raviv et al. |
| 5,046,504 | A | 9/1991 | Albert et al. |
| 5,101,833 | A | 4/1992 | Schmid |
| 5,284,152 | A | 2/1994 | Portnuff et al. |
| 5,458,116 | A | 10/1995 | Eger |
| 5,803,084 | A * | 9/1998 | Olson ............ 600/512 |
| 6,226,542 | B1 | 5/2001 | Reisfeld |
| 6,226,543 | B1 | 5/2001 | Gilboa et al. |
| 6,230,048 | B1 | 5/2001 | Selvester et al. |
| 6,301,496 | B1 | 10/2001 | Reisfeld |
| 6,385,476 | B1 | 5/2002 | Osadchy et al. |
| 6,389,310 | B1 * | 5/2002 | Demonceau et al. ......... 600/512 |
| 6,438,409 | B1 | 8/2002 | Malik et al. |
| 6,456,867 | B2 | 9/2002 | Reisfeld |
| 6,546,271 | B1 | 4/2003 | Reisfeld |
| 6,694,178 | B1 | 2/2004 | Soula et al. |
| 6,721,593 | B2 | 4/2004 | Anderson et al. |
| 6,754,523 | B2 | 6/2004 | Toole |
| 6,884,218 | B2 | 4/2005 | Olson |
| 6,920,350 | B2 | 7/2005 | Xue et al. |
| 6,937,899 | B2 | 8/2005 | Sheldon et al. |
| 7,010,349 | B2 | 3/2006 | Conley et al. |
| 2003/0028119 | A1 | 2/2003 | Xue et al. |
| 2003/0045805 | A1 | 3/2003 | Sheldon et al. |
| 2003/0083587 | A1* | 5/2003 | Ferek-Petric ................. 600/512 |
| 2004/0111021 | A1 | 6/2004 | Olson |
| 2004/0116982 | A1 | 6/2004 | Conley et al. |
| 2005/0209525 | A1* | 9/2005 | Bojovic et al. ................. 600/512 |

OTHER PUBLICATIONS

Rob MacLeod et al. "Report of the first visualization of the reconstructed electrocardiographic display symposium" Journal of Electrocardiology Table of Contents; ECG Imaging—p. 385 Abstract; "Fig. 3—Ten-millisecond images of normal activation in a normal human heart . . . "; vol. 38, No. 4, Oct. 2005.

Charles W. Olson "The Overlooked Utility of a 3D Cardiographic Display". 6 pages, U.S. Copyright Office registration TXU 913-733. Aug. 16, 1999 (2 pages).

Charles W. Olson "A New 3D Vector Cardiograph" 10 pages, U.S. Copyright Office registration TXu 913-345, Aug. 16, 1999 (2 pages).

Charles W. Olson "3D Vectorcardiographic Display" pp. 1-25, 86-111, U.S. Copyright Office registration TXu 913 732. Aug. 16, 1999 (2 pages).

Charles W. Olson "3D Vector Cardiographic Display Training Program" pp. 1-25, 139-164, U.S. Copyright Office registration TXu-1-102-488, May 12, 2003 (2 pages).

Charles W. Olson "T-Wave Analysis" First 25 pages, Last 25 pages U.S. Copyright Office Registration TXu 1-150-475 Dec. 17, 2003 (2 pages).

David G. Strauss et al. "Vectorcardiogram synthesized from the 12-lead electrocardiogram to image ischemia". ScienceDirect, Journal of Electrocardiology. (2009) (8 pages).

Clifton, III et al., "Direct Volume Display Devices", IEEE Computer Graphics & Applications, Jul. 1993.

* cited by examiner

```
Statistics of Critical Measurements
Measurement              Value    Zscore Maximum QRS Ampl.       .966 mv   -1.07
Duration in ms           84 ms    -0.33
Azimuth Angle at max    -39 deg   -0.84
Elevation Ang.at max     40 deg    1.17
Narrowness of Vectgr.   1.06       1.78
Initial Azimuth Ang.     28 deg   -0.25
Initial Elevat. Ang.     21 deg    0.61
T-wave Max. Ampl        .235 mv   -1.08
T-wave Azimuth at Max    60 deg    0.32
T-wave Elevat. at Max     0 deg   -1.50
```
{ 66

Probable Patient Diagnosis:
Norm: Norm

LOCATION AND DISPLAYING AN ISCHEMIC REGION FOR ECG DIAGNOSTICS

CROSS-REFERENCE TO RELATED APPLICATIONS

This application claims the benefit of priority to U.S. Provisional Patent Application Ser. No. 61/169,047 by Olson entitled "DISPLAY FOR THE EVALUATION AND MONITORING OF AN ISCHEMIC EVENT" filed on Apr. 14, 2009 and is a continuation in part of U.S. patent application Ser. No. 11/411,365 by Olson filed on Apr. 25, 2006 and published on Nov. 16, 2006 as U.S. Patent Application Publication No. US 2006/0258947 A1, entitled "DISPLAY FOR ECG DIAGNOSTICS", which claims priority to U.S. Provisional Patent Application Ser. No. 60/674,789 by Olson entitled "DISPLAY FOR ECG DIAGNOSTICS" filed on Apr. 25, 2005, the entire contents of each of which are incorporated by reference herein.

BACKGROUND

1. Technical Field

The present disclosure relates to a diagnostic display for an electrocardiograph (ECG).

2. Related Prior Art

Three-dimensional (3D) electronic presentation of clinical ECG interpretations are known in the art. Increasingly, physicians are performing clinical ECG interpretations electronically. The change from paper to electronic presentation provides the potential for the physician to receive such immediate decision support as the required educational software is developed. This might appropriately be considered as receiving a self-guided "second opinion" regarding a clinical decision.

However, when physicians are uncertain whether to accept or alter automated diagnostic statements, there is no immediately available support for their decision.

Additionally, it is known in vector cardiography that the angle of an ischemic region in the heart formed following an ischemic event is obtained from the Azimuth and Elevation angles of the difference vector or the direct vector. This vector is the sum of the electrical vectors of the effect of the ischemia which is prevalent over an area of the heart which has been deprived of oxygen due to the blockage of the coronary artery. The angle of the ischemia can be used to compute the location in the heart where the center of the ischemic effect is located and in that way alert the medical staff where to look for the affected coronary artery.

However, since the axis of the heart is offset from the vertical and horizontal positions of the body, i.e. the vertical and horizontal axes of the torso, and the vector location of the ischemic vector is in relationship to the body coordinates, it is difficult for the attending physician to mentally visualize the precise location of the ischemic region from the ECG measurements, which are taken with respect to the body positions. It is necessary for the attending physician to mentally visualize the precise location of the ischemic region.

SUMMARY

The present disclosure relates to a medical display for analyzing heart signals, that includes a cardiographic display which displays at least a segment of an, or an entire, electrocardiograph (ECG) heart signal of a patient having a magnitude and location in vector format within a single three-dimensional (3D) coordinate system, e.g., X, Y, Z, (vectorcardiograph) sampled at incremental time intervals. The display operatively communicates with a central processing unit (CPU) that implements a diagnostic algorithm to permit a user to selectively and visually display a comparison of the at least a segment of the patient ECG signal with at least one known display in vector format within a single three-dimensional (3D) coordinate system. The known display(s) consist of a normal cardiac condition (including a patient's prior or current normal condition) or an abnormal or reference cardiac condition that includes at least one of a patient prior or current cardiac condition, a myocardial infarction condition, a hypertrophic condition, an ischemic condition, and a bundle branch block condition. The known displays in vector format are stored in a known cardiac conditions database, which in turn is stored in a memory operatively coupled to the CPU. The cardiographic display operatively communicates with the CPU to allow a user to selectively display critical measurements of at least one of the at least a segment of the patient ECG signal, obtained via patient monitoring, and the known display(s) in vector format.

The algorithm may compare the patient ECG critical measurements to the critical measurements stored in the cardiac conditions database and the CPU may operatively communicate with the cardiographic display to visually display the results of the comparison as a normal or abnormal condition. In addition, the cardiographic display may operatively communicate with the CPU to allow a user to selectively display an overlay over the vectorcardiograph patient ECG, with the overlay including at least one of a 3D representation of a heart, a representation of coronary arteries over a projection of a heart, and a 3D vectorcardiograph of a cardiac condition. The at least a segment of the patient ECG signal includes at least one of a P-wave interval, PR interval, QRS interval, QT interval and T-wave interval.

The present disclosure relates also to a medical display for analyzing heart signals, which includes a cardiographic display which displays at least a segment of an electrocardiograph (ECG) heart signal of a patient having a magnitude and location in vector format within a single three-dimensional (3D) coordinate system (vectorcardiograph) sampled at incremental time intervals. The display operatively communicates with a central processing unit (CPU) that implements an algorithm to permit a user to selectively and visually convert and display the at least a segment of the patient ECG into at least a first color coded projection of a time sequence of the at least a segment of an ECG heart signal. The color coded time sequence projection corresponds to a lead signal associated with the magnitude and location of the vector signal. The color coded time sequence represents a time line duration of the vector signal.

The present disclosure relates also to a method for analyzing heart signals, which includes the step of implementing the algorithm to permit a user to selectively and visually display a comparison of the electrocardiograph (ECG) heart signal of a patient having a magnitude and location in vector format within a single three-dimensional (3D) coordinate system (vectorcardiograph) sampled at incremental time intervals with at least one known display in vector format within a single three-dimensional (3D) coordinate system. The known display(s) consist of a normal cardiac condition (including a patient's prior or current normal condition) or an abnormal or reference cardiac condition that includes at least one of a patient prior or current cardiac condition, a myocardial infarction condition, a hypertrophic condition, an ischemic condition, and a bundle branch block condition. As previously indicated, the known displays in vector format are stored in the known cardiac conditions database, which in turn is stored in the memory.

The step of implementing the algorithm may further include implementing the algorithm to allow the user to selectively display the critical measurements of at least one of the patient ECG and the known display in vector format. The step of implementing the algorithm further may also include implementing the algorithm to allow a user to compare the patient ECG critical measurements to critical measurements stored in a database and to operatively communicate with the cardiographic display to visually display the results as a normal or abnormal condition. The step of implementing the algorithm may further include implementing the algorithm to allow a user to selectively display an overlay over the vectorcardiograph patient ECG. The overlay includes at least one of a 3D representation of a heart, a representation of coronary arteries over a projection of a heart, and a 3D vectorcardiograph of a cardiac condition. The at least one segment of a patient ECG signal includes at least one of a P-wave interval, PR interval, QRS interval, QT interval and T-wave interval.

The present disclosure relates also to a method for analyzing heart signals which includes the step of implementing an algorithm to permit a user to selectively and visually convert and display at least a segment of an ECG into a color coded projection of a time sequence of the at least a segment of an ECG heart signal. The color coded time sequence projection corresponds to a lead signal associated with the magnitude and location of the vector signal. The color coded time sequence represents a time line duration of the vector signal.

The present disclosure also advances the state of the art by disclosing a method for locating an ischemic region in the heart of a subject. The method includes the steps of: establishing three dimensional coordinates axes with respect to the torso of the subject as a reference; establishing as a reference a multi-dimensional representation of the heart defining at least three dimensional coordinate axes of the heart, the multi-dimensional representation defining at least the base of the heart and a middle section of the heart; and orienting the three dimensional coordinate axes of the heart from an initial position offset with respect to the three dimensional coordinates with respect to the torso of the subject to an imaginary position wherein at least one axis of the heart is parallel to or coincident with at least one of the three dimensional coordinate axes with respect to the torso of the subject.

The present disclosure relates also to a medical display for locating an ischemic region in the heart of a subject. The display portrays the location of the ischemic region via: three dimensional coordinates axes established with respect to the torso as a reference; a multi-dimensional representation of the heart established as a reference defining at least three dimensional coordinate axes of the heart, the multi-dimensional representation defining at least the base of the heart and a middle section of the heart; and the three dimensional coordinate axes of the heart being oriented from an initial position offset with respect to the three dimensional coordinates with respect to the torso of the subject to an imaginary position wherein at least one axis of the heart is parallel to or coincident with at least one of the three dimensional coordinate axes with respect to the torso of the subject.

BRIEF DESCRIPTION OF THE DRAWINGS

The subject matter regarded as the embodiments is particularly pointed out and distinctly claimed in the concluding portion of the specification. The embodiments, however, both as to organization and method of operation, together with objects, features, and advantages thereof, may best be understood by reference to the following detailed description when read with the accompanying drawings, wherein similar reference characters denote similar elements throughout the several views, in which:

FIG. 5 illustrates the statistics of critical parameters compared to a normal heart as found in 50 patients having a catheter verification of normality;

DETAILED DESCRIPTION

U.S. Pat. No. 5,803,084 by Olson, issued Sep. 8, 1998, entitled "THREE DIMENSIONAL VECTOR CARDIOGRAPHIC DISPLAY AND METHOD FOR DISPLAYING SAME" and U.S. Pat. No. 6,884,218 B2 by Olson, issued Apr. 26, 2005, entitled "THREE DIMENSIONAL VECTOR CARDIOGRAPH AND METHOD FOR DETECTING AND MONITORING ISCHEMIC EVENTS" are incorporated by reference herein in their entirety.

Figure 1:
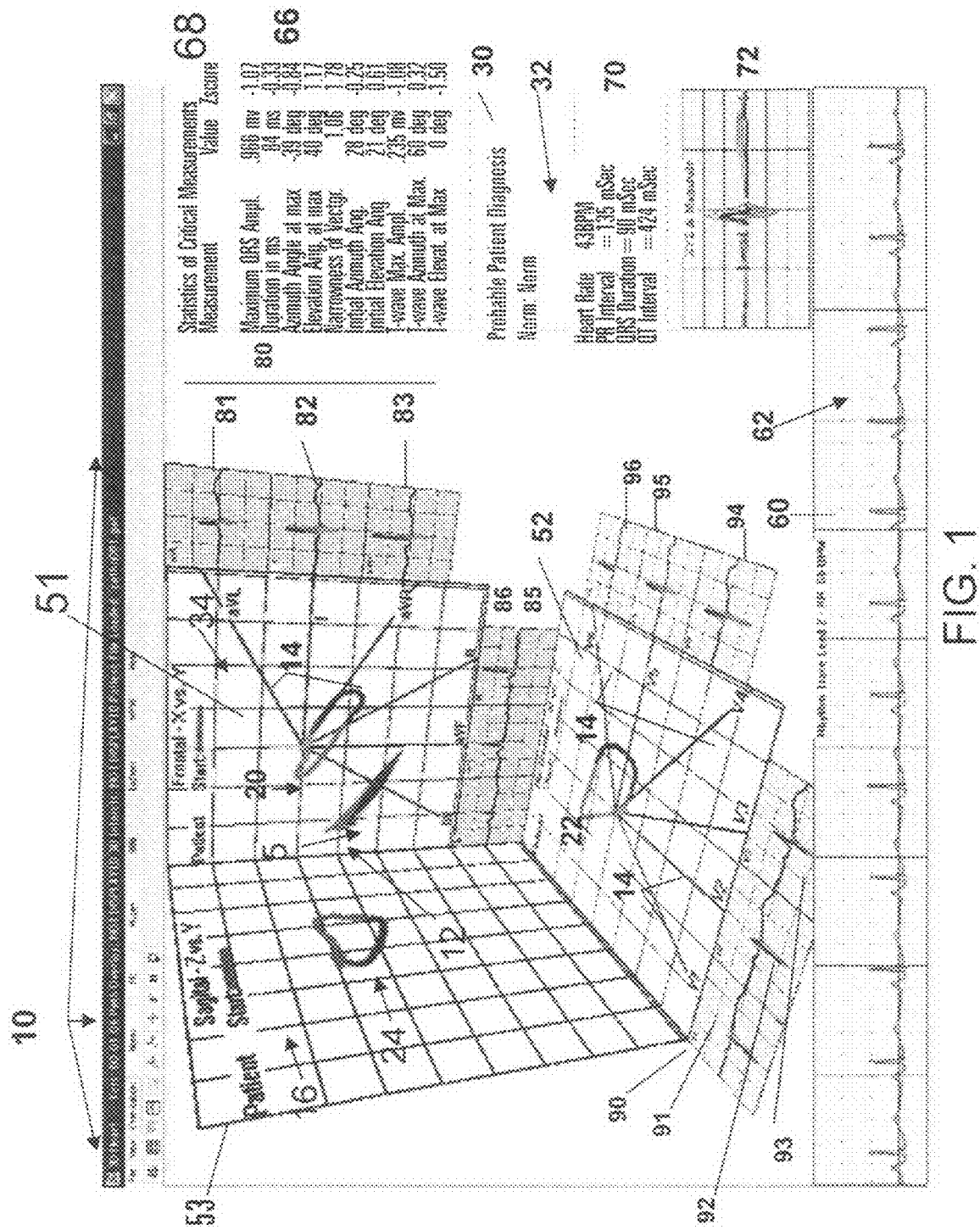
FIG. 1 illustrates a first operating display of a patient file in a 3D vectorcardiograph in which patient files are selected from a file menu box according to a method of the present disclosure for displaying an ECG signal.

FIG. 1 illustrates a medical display or cardiographic diagnostic display 10 for displaying at least one segment of, or an entire, electrocardiograph (ECG) heart signal 12 having a magnitude and location in vector format within a single three-dimensional (3D) coordinate system (e.g., X, Y, Z as shown) which is sampled at incremental time intervals according to the present disclosure. More particularly, the display 10 displays and separates cardiac conditions into recognizable patterns of 3D vectors 14. The segments of the ECG signal 12 vector patterns may include a P-wave segment, a QRS segment, or a T-wave vector segment or combinations thereof. However, for illustrative purposes only, FIGS. 1, 2, 8-13, and 15-16 display a QRS segment or portion of a lead signal. As described below with respect to FIGS. 17-18, a color code map is used to identify the time sequence of the lead vectors 14. The display 10 is a top level display which may be utilized for making a substantially immediate probable diagnosis 30. The probable diagnosis 30 is shown in right middle region 32 of the display 10. The probable diagnosis 30 is determined as a result of implementation of a machine algorithm as discussed below with respect to FIG. 3. In a large area 34, a 3D picture of the ECG of the patients' heart 5 is shown with planar projections or vector loops 20, 22 and 24 projected as time sequences, in color-coded form, into the three planes: Frontal 51, Horizontal 52 and Sagital 53, respectively, as first color-coded projections. The lead vectors 14 include vector lead aVL, vector lead 1, vector lead aVR, vector lead II, vector lead aVF, and lead vector III associated with the frontal plane 51, and vector lead V1, vector lead V2, vector lead V3, vector lead V4, vector lead V5 and vector lead V6 associated with the horizontal plane 52.

The first color-coded frontal planar projection or vector loop 20 in turn is projected into lead projections as second color-coded projection 81 corresponding to vector lead aVL, second color-coded projection 82 corresponding to vector lead I, and second color-coded projection 83 corresponding to vector lead aVR, the foregoing each displayed on a vertical side panel 80 associated with frontal plane 51, and also as second color-coded projection 86 corresponding to vector lead II, second color-coded projection 87 corresponding to vector lead aVF, and second color-coded projection 88 corresponding to vector lead III, the foregoing each displayed on a vertical lower panel 85 associated with frontal plane 51.

The first color-coded frontal planar projection or vector loop 22 in turn is projected into lead projections as second color-coded projection 91 corresponding to vector lead V1, second color-coded projection 92 corresponding to vector lead V2, and second color-coded projection 93 corresponding to vector lead V3, the foregoing each displayed on a horizontal panel 90 associated with horizontal plane 52, and also as second color-coded projection 94 corresponding to vector lead V4, second color-coded projection 95 corresponding to vector lead V5, and second color-coded projection 96 corresponding to vector lead V6, the foregoing each displayed on a horizontal panel 98 associated with horizontal plane 52.

Although those skilled in the art recognize the character of a normal heart in the form of the 3D picture 5, as discussed below with respect to FIGS. 12 and 14, a 3D picture of a wide variety of disease states can be over laid to facilitate and enhance diagnosis. As defined herein, an overlay is construed as, but not limited to, the following examples: a top over a bottom view, a dual screen or side by side illustration, or a phantom illustration. The embodiments are not limited in this context.

As further confirmation of the result, a chart of statistical information 66 is shown in upper right region 68. The chart of statistical information 66 itemizes the critical parameters of the 3D measurement and presents the corresponding Z-scores. Lower region 62 of the display 10 may include a rhythm strip 60 which provides additional information relating to rhythmic types of abnormalities. Also projections onto the 12 Leads are shown.

The 3D image of the heart 5 and the surrounding background in 3D can be rotated and expanded to view any part of the image of the heart 5 in greater detail.

Figure 2:
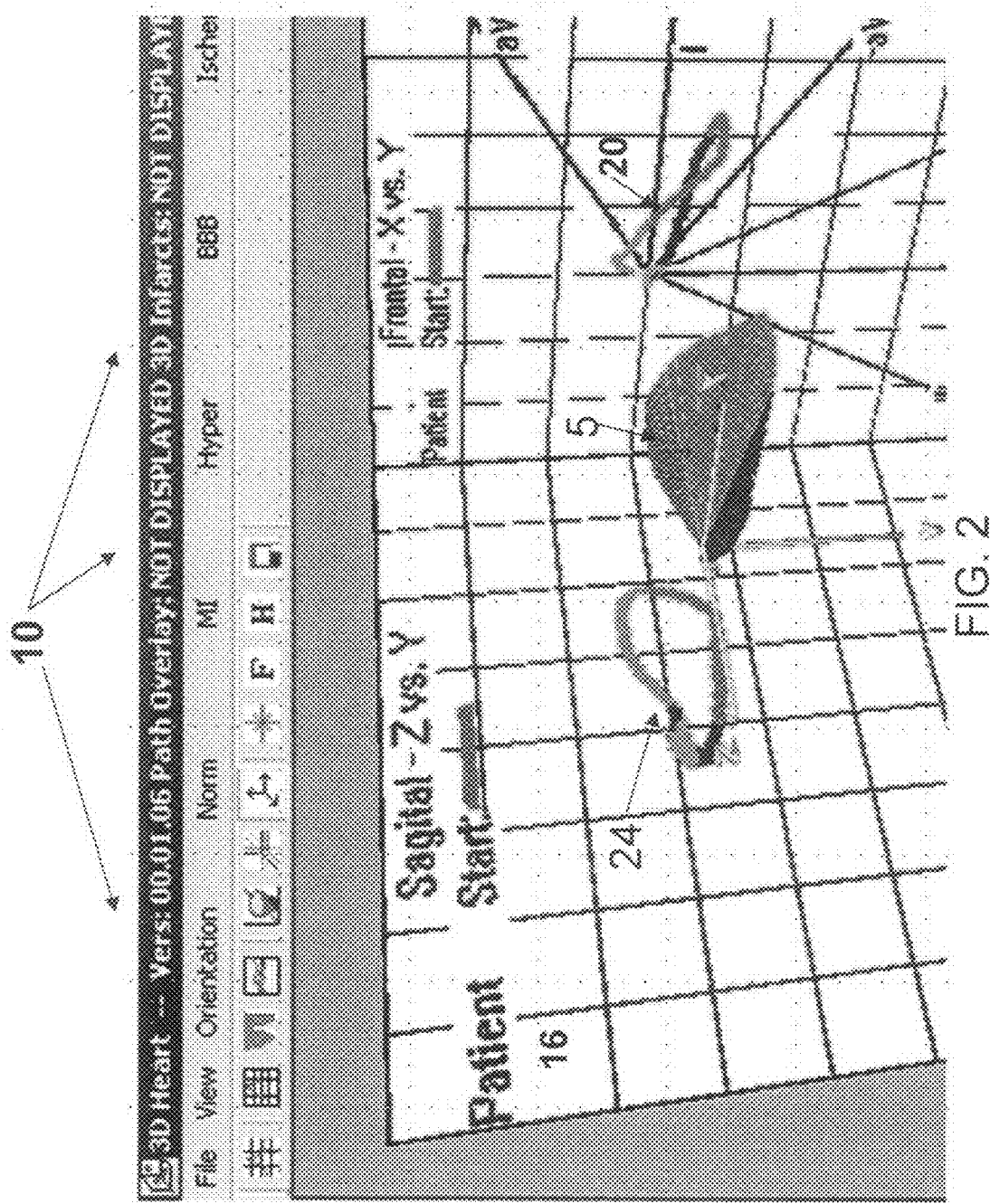
FIG. 2 illustrates an expansion of the upper left portion of the initial display showing a frontal and sagital projection of a 3D vector diagram seen at the origin of the display.

FIG. 2 illustrates an expansion of upper left portion 16 of the initial display 10 showing a frontal and sagital projection of the 3D vector diagram 12. The origin of the ECG vectorcardiograph signal display 12 is the intersection of X, Y and Z axes, i.e., at the origin of the X, Y, and Z axes.

Figure 3:
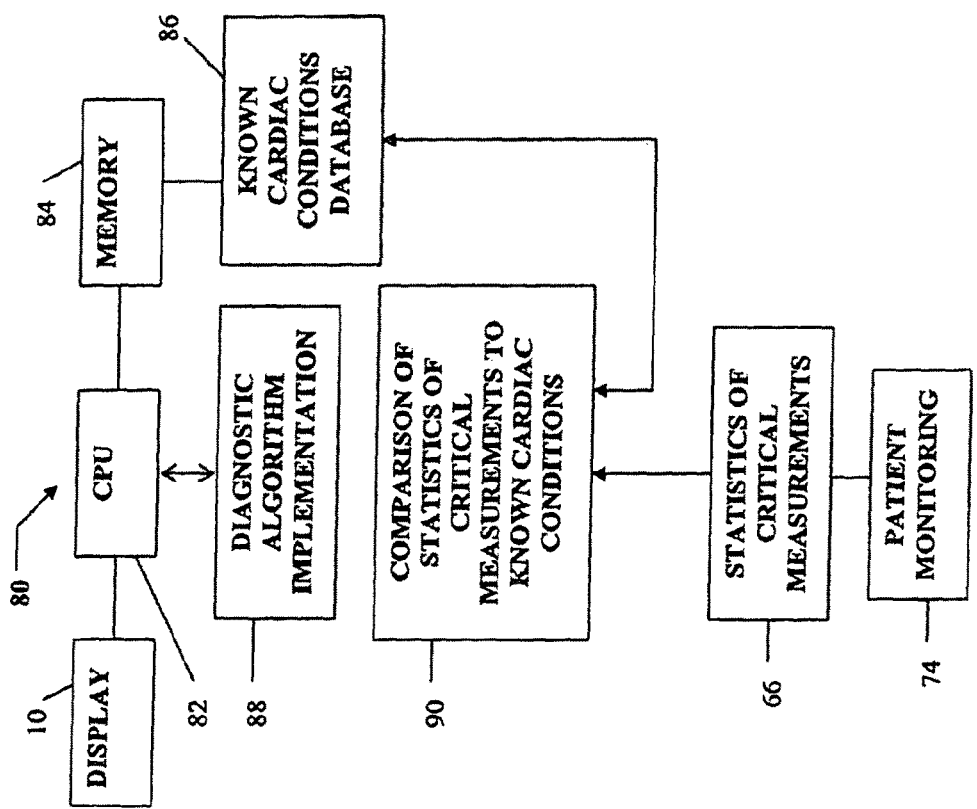
FIG. 3 illustrates a schematic diagram of a medical display system according to the present disclosure.

FIG. 3 is a schematic diagram of a medical display system and method 80 according to the present disclosure. More particularly, a central processing unit (CPU) 82 is operatively coupled to the display 10 and to a memory 84. The memory 84 stores a known cardiac conditions database 86. The CPU 82 implements a diagnostic algorithm 88 causing a comparison 90 of the statistics of critical measurements 66 to the known cardiac conditions stored in the known cardiac conditions database 86. The statistics of critical measurements 66 are derived from patient monitoring 74, in which the actual patient cardiac measurements are operatively communicated to the CPU 82 during the steps of comparing 90 to the known cardiac conditions in the database 86 resulting from the implementation 88 of the diagnostic algorithm.

Figure 4A:
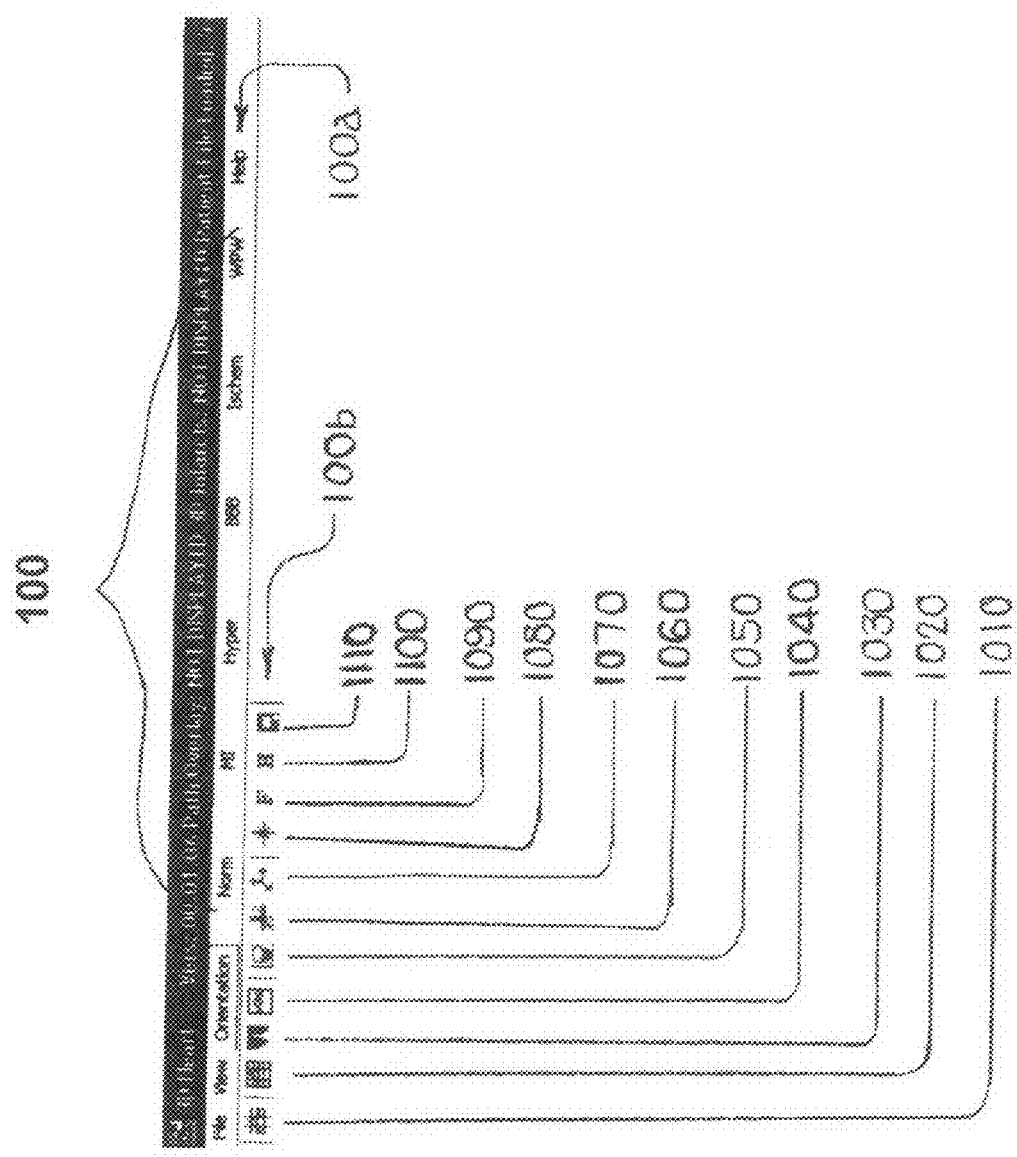
FIG. 4A is a detailed view of the display of FIG. 1 illustrating specific tool bar functions of the display.
Figure 4B:
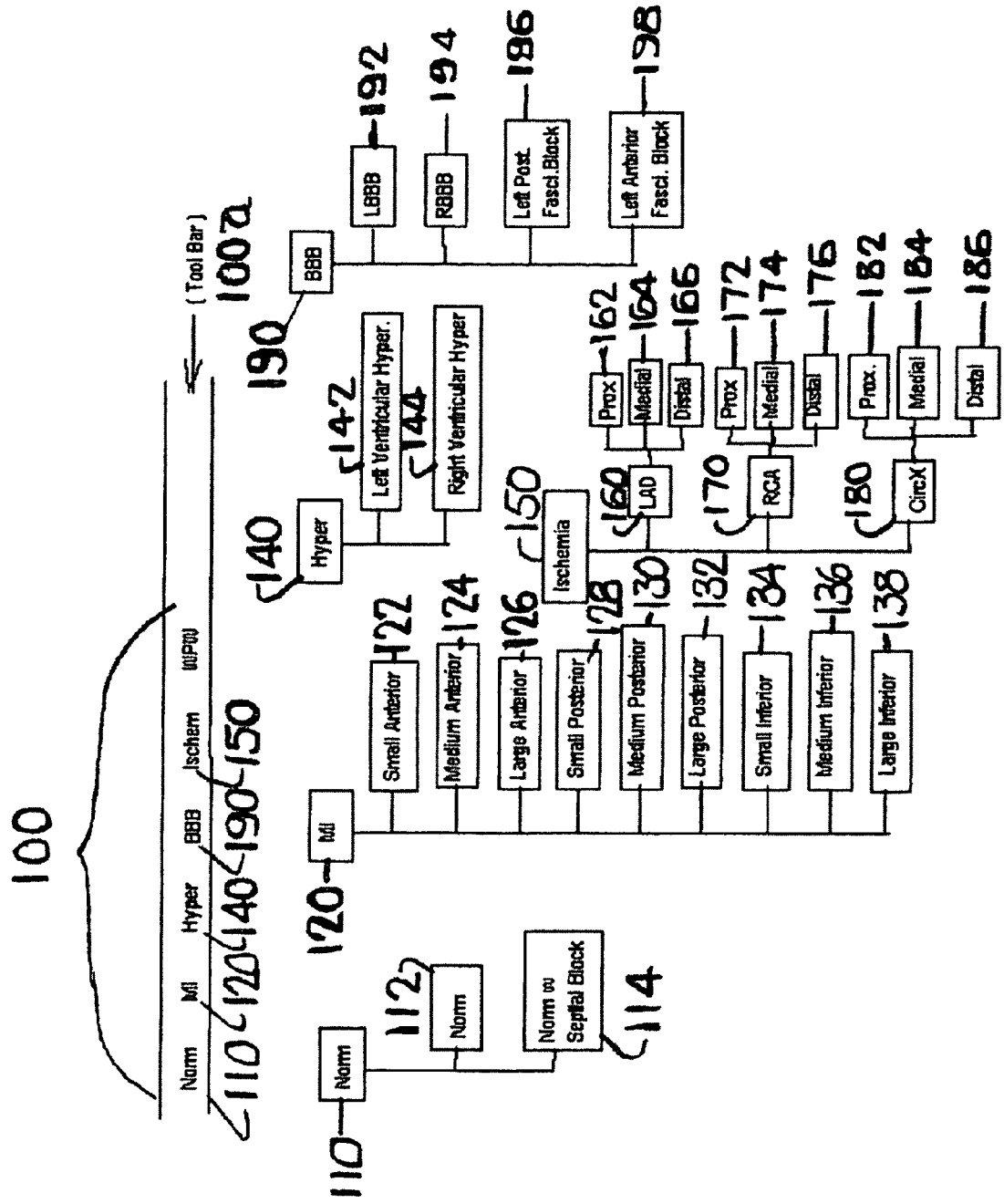
FIG. 4B illustrates tool bar selections of disease states of the general population for comparison with a patient's ECG.

Referring to FIGS. 4A and 4B, FIG. 4A is a detailed view of the display 10 illustrating specific tool bar functions of the display 10. More particularly, the display 10 includes a first toolbar 100a having a group of selections 100 which includes cardiac conditions 102 (see FIG. 4B). In addition, the selections 100 include cardiac condition 155 which represents Wolfe-Parkinson-White Syndrome.

A second toolbar 100b includes a series of icons. As illustrated by way of example in FIG. 4A, from left to right, a first icon 1010 represents a command to open a patient file for input. A second icon 1020 represents the selection of normal 12 lead ECG display. A third icon 1030 represents a Mercator projection command. A fourth icon 1040 represents the display of a full ECG heart beat showing P-wave, QRS, and T-wave with fiducial bars to show the start and end of these waves. A fifth icon 1050 superimposes or overlays an image of the heart 5 over the 3D vector diagram 12. A sixth icon 1060 represents an overlay command of a version of the 3D ECG associated with the particular disease or cardiac condition 100 chosen. A seventh icon 1070 represents an X, Y, Z coordinates command. An eighth icon 1080 resets the display 10 to a default orientation. A ninth icon represents a frontal plane "F" command. A tenth icon 1090 represents a horizontal plane "H" command. Finally, an eleventh icon 1100 represents a command to save the present orientation. Other icons may be added as desired.

FIG. 4B illustrates the tool bar selections 100 of the cardiac conditions 102 of the general population for comparison with an ECG 12 of a patient. For comparison purposes, the cardiac conditions 102 include normal conditions 110. The normal conditions 110 are sub-divided into entirely normal states 112 and normal states with septal blockage 114.

The cardiac conditions 102 selectable by the tool bar 100 also include myocardial infarctions (MI) 120 which are sub-categorized into small, medium and large anterior states 122, 124 and 126, respectively; small, medium and large posterior states 128, 130 and 132, respectively; and small, medium and large interior states 134, 136 and 138, respectively.

The cardiac conditions 102 also include hypertrophy 140 which is sub-categorized into left ventricular hypertrophy 142 and right ventricular hypertrophy 144. In addition, ischemia conditions 150 are sub-divided into three major sub-divisions: left anterior descending (LAD) 160; right coronary artery (RCA) 170; and circumflex (CircX) 180. The sub-division LAD 160 is sub-categorized into proximal, medial and distal 162, 164, and 166, respectively. Similarly, the sub-division RCA 170 is also sub-categorized into proximal, medial and distal 172, 174, and 176, respectively. As well, the sub-division CircX 180 is sub-categorized into proximal, medial and distal 182, 184, and 186, respectively.

Finally, the cardiac conditions 102 also include bundle branch block (BBB) states 190 which are sub-categorized into: left bundle branch block (LBBB) 192; right bundle branch block (RBBB) 194; left posterior fascicular block 196 and left anterior fascicular block 198.

The tool bar selections 100 provide drop menus of a wide variety of cardiac condition disease states 102 that can be used for comparison with the ECG of a patient. The 3D ECG of the disease state chosen is over laid on top of the patient's 3D ECG for a simple and rapid comparison.

Therefore, the tool bar selections 100 on the display 10 enable display of at least two of the cardiac conditions 102, e.g., the normal cardiac conditions 110, the myocardial infarction (MI) condition 120, the hypertrophy conditions 140, the ischemic conditions 150, and the bundle branch block (BBB) conditions 190.

The user, such as a doctor, may display the critical measurements 66 of at least one of the recognizable patterns of 3D vectors 14. The user may compare the display of critical measurements 66 to statistical information for at least one of the cardiac conditions 102. The cardiac condition 102 may include an abnormality such as the myocardial infarction (MI) condition 120, the hypertrophy conditions 140, the ischemic conditions 150, and the bundle branch block (BBB) conditions 190.

FIG. 5 illustrates the statistics of critical parameters or measurements 66 compared to a normal heart as found in 50 patients having a catheter verification of normality. The right side of the display shows the Statistics of Critical Measurements 66. The measured value for the patient is shown as the Value. The Zscore is the number of standard deviations of the patient's reading from a normal mean or median value. The Zscore is an example of an important measurement made readily available to a user of the cardiographic diagnostic display 10. As defined herein, a user may be a human such as a doctor or physician, a nurse, or medical technician or other skilled professional or a user may be a machine programmed to perform a diagnostic function by visual observation or selective manipulation of the medical displays or methods described herein.

The probable patient diagnosis 30 is shown at the bottom. The Statistics of Critical Measurements 66 may include, but are not limited to, the Maximum QRS Amplitude, the Duration in milliseconds (ms), the Azimuth Angle at maximum, the Elevation Angle at maximum, the Narrowness of width of the 3D vectorgraph compared to the measurement of the QRS amplitude, the Initial Azimuth Angle, the Initial Elevation Angle, the T-wave Maximum Amplitude, T-wave Azimuth at Maximum, T-wave Elevation at Maximum. Other measurements may also be added and may be part of a sub-menu and/or a user-specific display variable.

Figure 6:
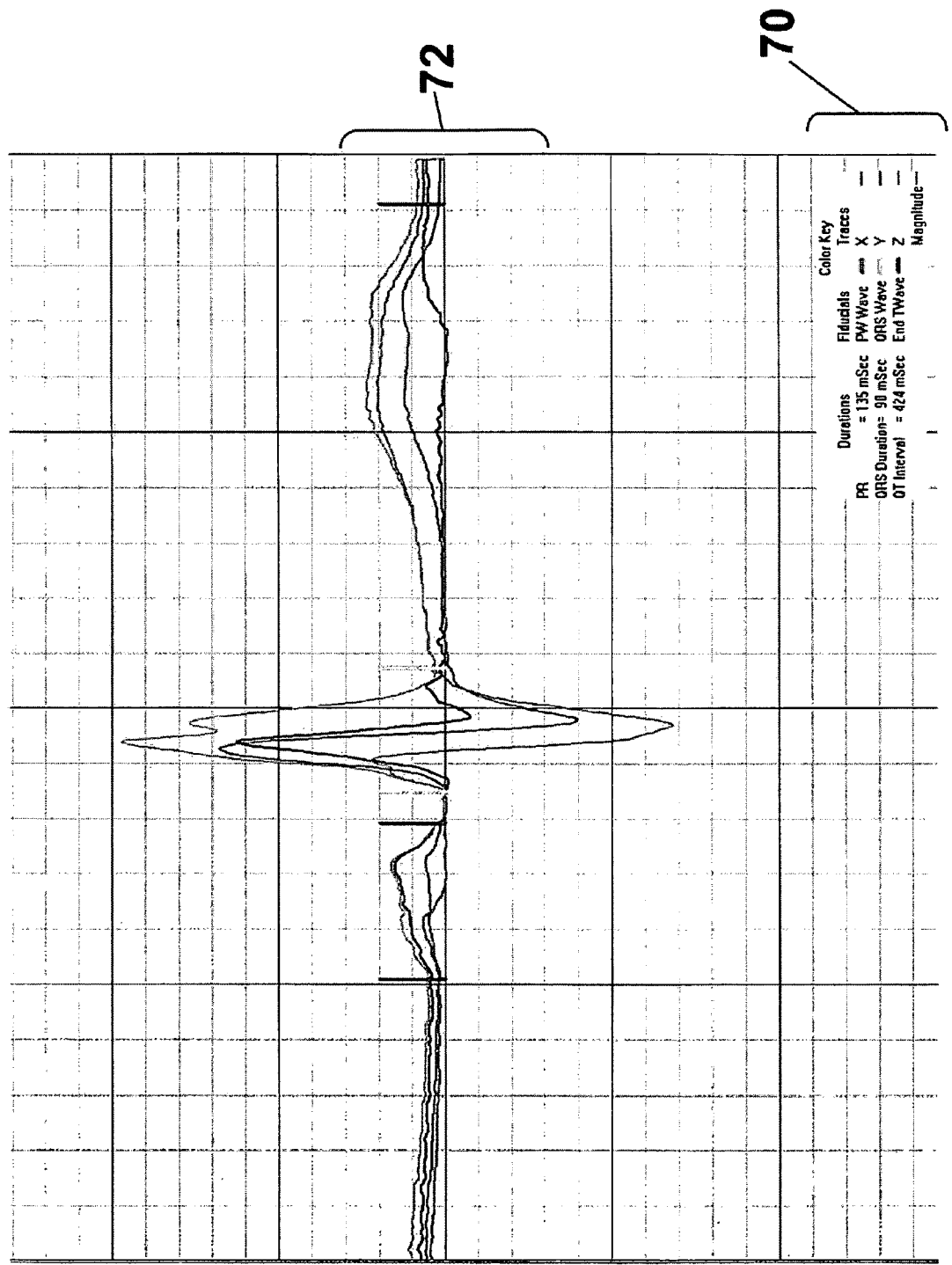
FIG. 6 illustrates the validity of fiducial points that have been automatically selected by a software algorithm according to the present disclosure.

FIG. 6 illustrates the validity of fiducial points 70 that have been automatically selected by a software algorithm according to the previous disclosure. The important measurements are also shown in this view. The fiducial selections, e.g., PW wave, QRS wave, and the End of the T wave, are shown. Also indicated at the bottom is the PR interval, QRS interval and the QT interval. FIG. 6 is an expanded version of the graphical plot 72 illustrated in the lower right-hand corner of FIG. 1. The expansion of the graphical plot in FIG. 1 can be rapidly selected by clicking on a corresponding symbol or marker on the tool bar 100 display, for example, the symbol icon 1040 illustrated in FIG. 4A.

Figure 7:
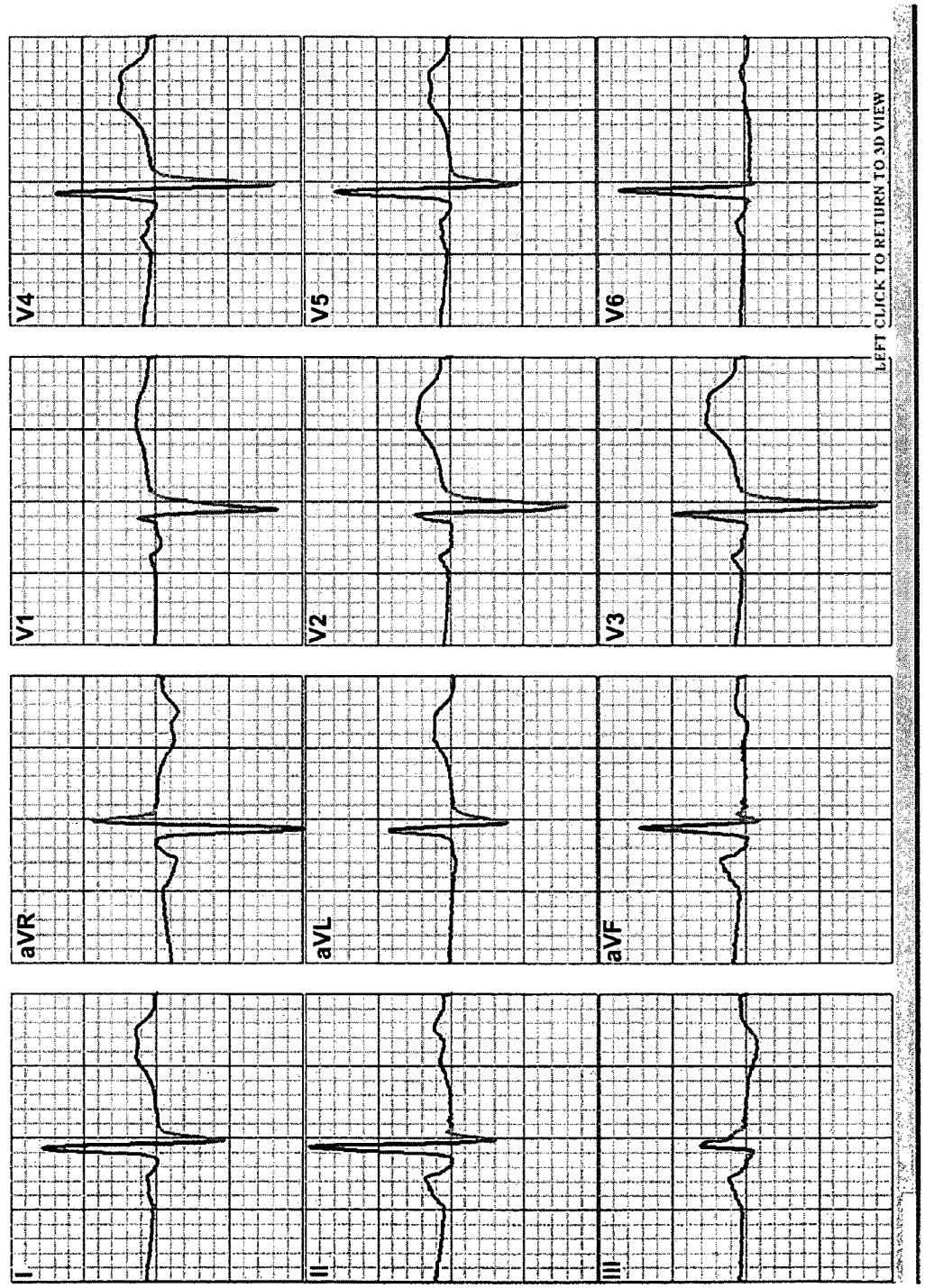
FIG. 7 illustrates a prior art 12 lead ECG display which can be displayed by the method of the present disclosure.

FIG. 7 illustrates a prior art 12 lead ECG display 76. By selecting a second function or sub-menu 1020 of the tool bar 100, a full screen display of patient data may be shown.

Figure 8:
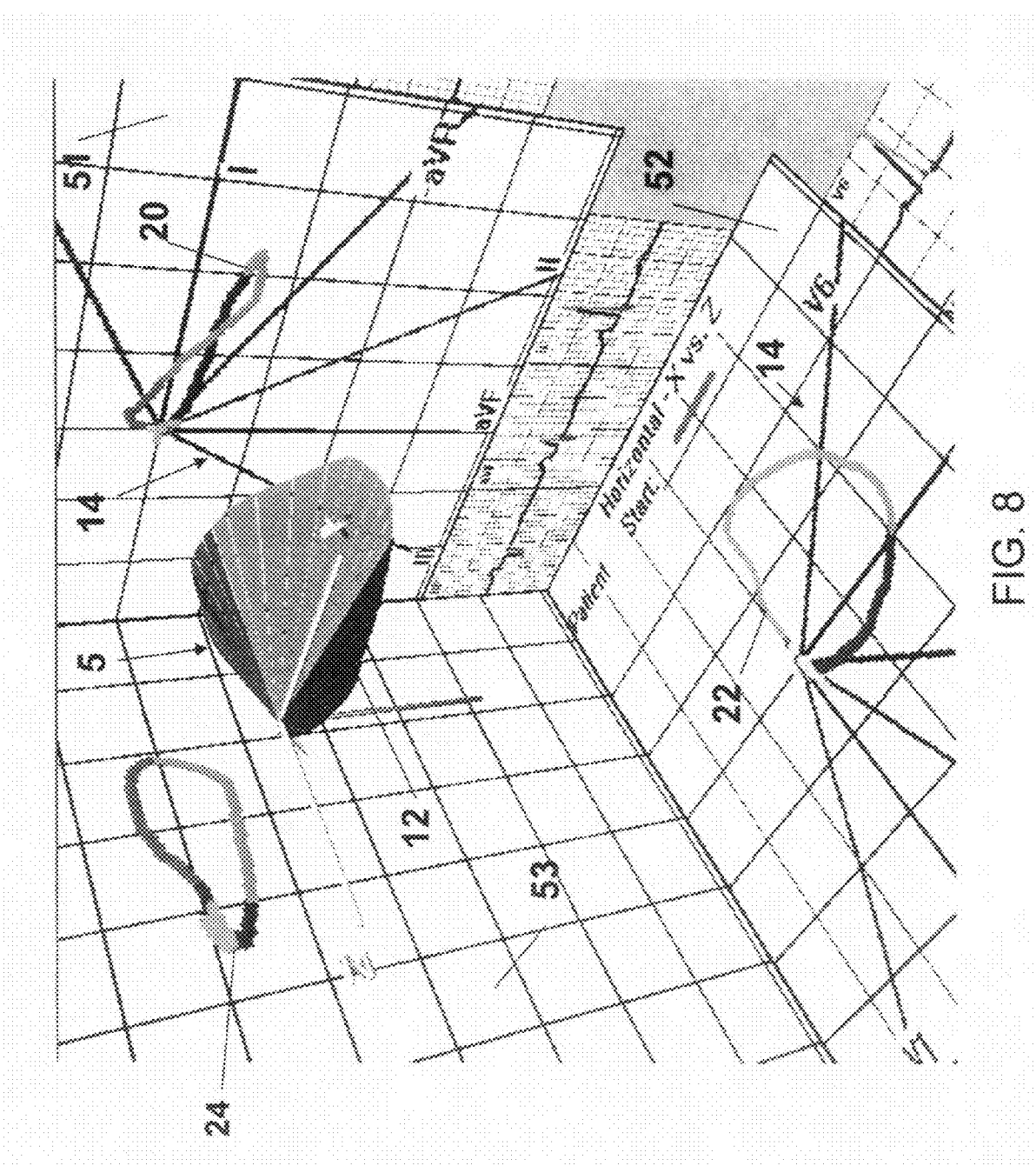
FIG. 8 illustrates an expanded view of the 3D vectorcardiograph of FIG. 1 showing more details.

FIG. 8 illustrates an expanded view of the 3D vectorcardiograph 12 of FIG. 1 showing more details for the same patient illustrated in FIG. 1. The 3D display 10 can be expanded and the display 10 rotated to show more detail of the patient data, and to provide an expanded angle of view. Optional X, Y and Z coordinate axes have been added to the 3D picture 10 to provide orientation of the ECG in the body of the patient (not shown). The X, Y and Z coordinate axes are selected by clicking on a tool bar symbol 1070 or sub-menu (not shown) showing the three axes.

Therefore, the display 10 displays one heart signal as X, Y and Z vector signals and the resultant magnitude of the signal Although an X, Y and Z coordinate system is illustrated in FIG. 8, other coordinate systems such as, but not limited to, cylindrical coordinate systems (e.g., r, .THETA., z) or spherical coordinates (e.g., r, .theta., .phi.) may also be applied. The embodiments are not limited in this context.

The X, Y and Z vector signals and the resultant magnitude of the signal are displayed to illustrate an estimate of at least one of P-wave interval, PR interval, QRS interval, QT interval and T-wave interval. For example, the resultant magnitude Mag.sub.vd of any signal can be determined by the following formula: Mag.sub.vd={square root over ((x.sup.2+y.sup.2+z.sup.2))} where x is the magnitude of the X-component of the 3D vectorcardiograph 12, y is the magnitude of the Y-component of the 3D vectorcardiograph 12, and z is the magnitude of the Z-component of the 3D vectorcardiograph 12, or in effect, x, y, and z are the orthogonal coordinates of the 3D vector 12.

Figure 9:
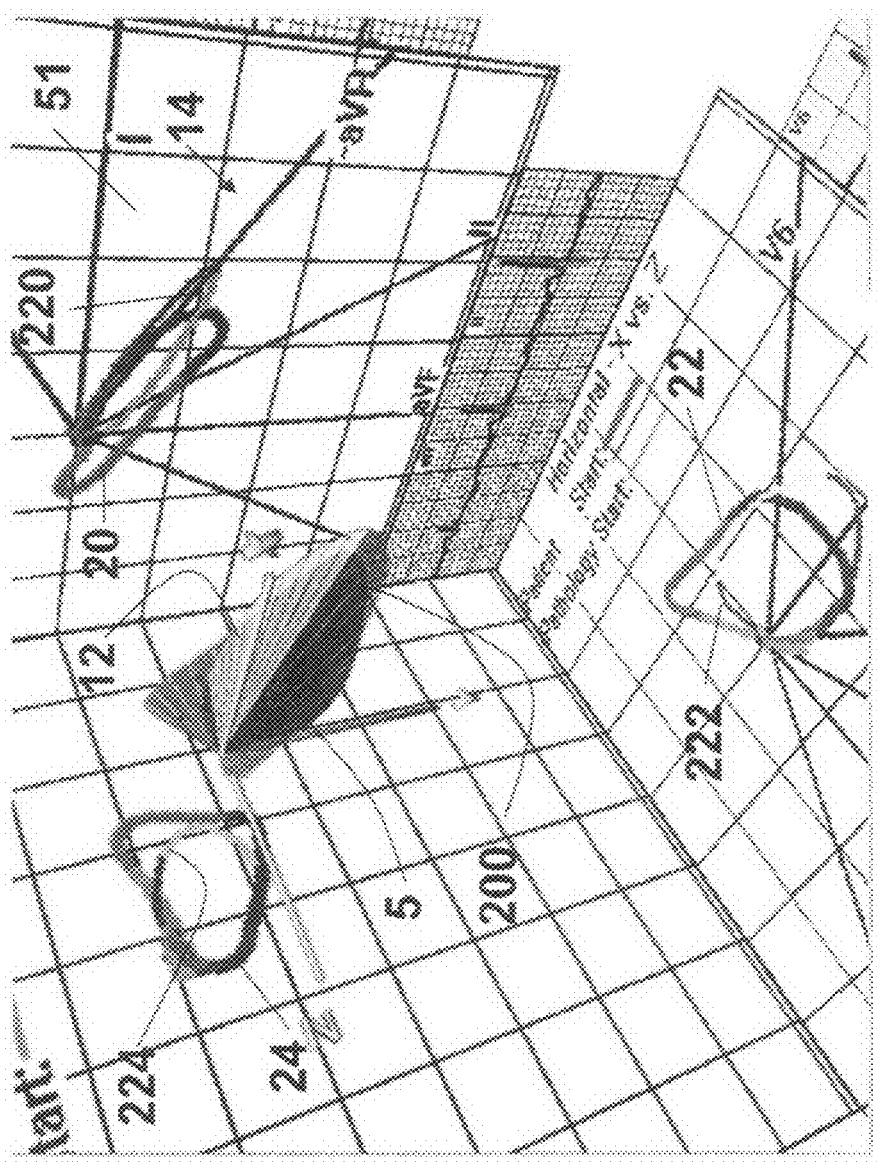
FIG. 9 illustrates an average of the critical parameters of the 50 patients having a normal heart overlaying the 3D vectorcardiograph of FIG. 8.

FIG. 9 illustrates an average 200 of the critical parameters of the 50 patients having a normal heart overlaying the 3D vectorcardiograph 12 of FIG. 8. The average 200 of 50 normals is over laid or compared to the previous patient data 12 both in the 3D display, and the three planes, illustrated as 220, 222 and 224 for the X, Y and Z axes, respectively. The color code for the normal master is light blue, brown, yellow and green. By selecting the tool bar symbol for a given over lay (e.g., icon 1060 in FIG. 4A), the 3D vectorcardiogram of the diagnosed disease is over laid the patient ECG. This is illustrated in, and discussed below with respect to, FIG. 13, which compares a vector cardiogram of a heart of normal patient to that of a heart of a patient having experienced a large anterior myocardial infarction.

FIG. 9 shows the advantages of using 3D patterns for recognizing and diagnosing heart conditions. The average 200 of 50 normal patients is used as a control to compare to the ECG 12 of the patient. Those skilled in the art may quickly and readily perceive a normal heart condition versus any give patient by matching the patient ECG 12 in timing size, duration and in the planar characteristics. The projected signals in the three planes 220, 222 and 224, respectively, may also be used to closely match the normal average 200.

Figure 10:
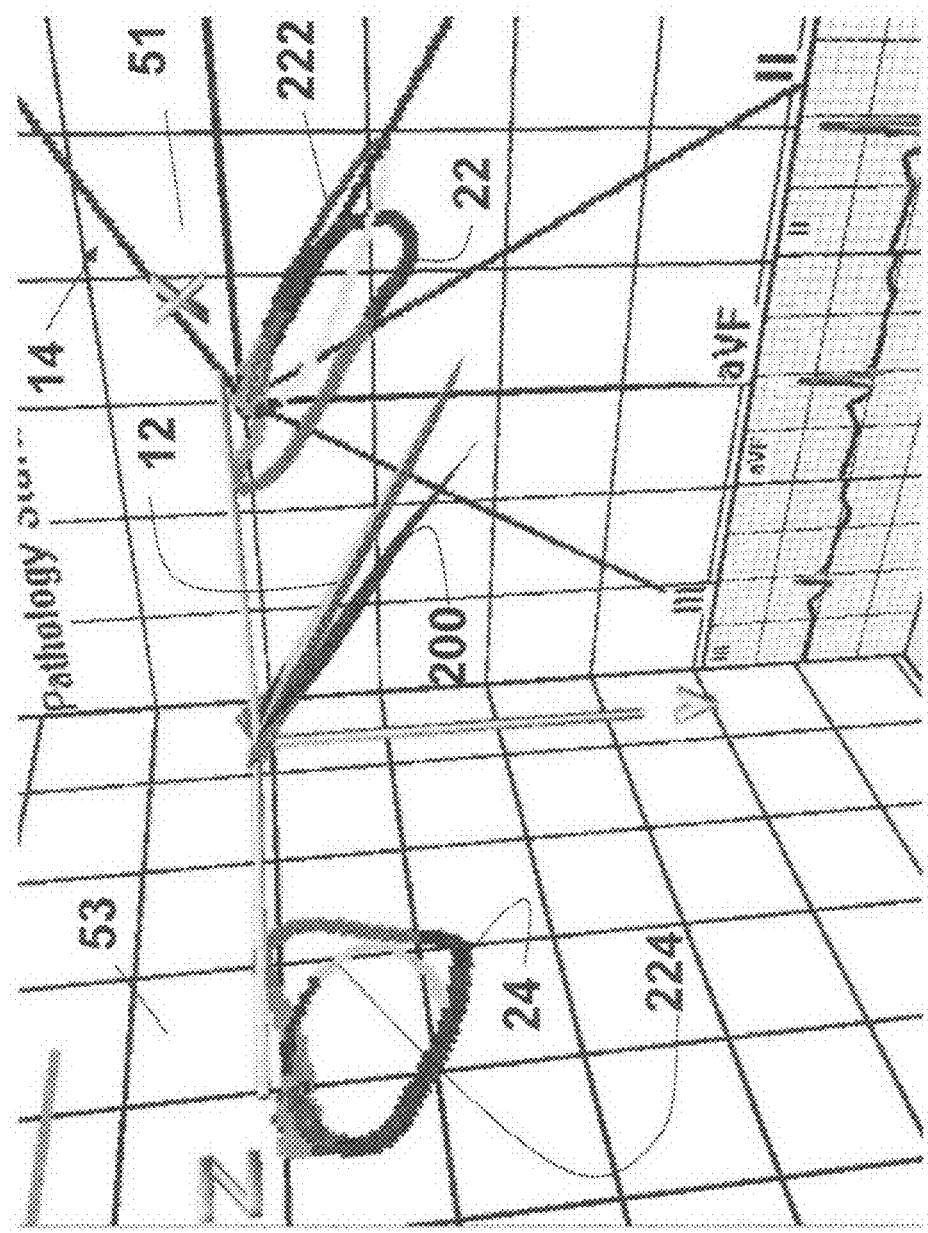
FIG. 10 illustrates a side or edge view of the 3D vectorcardiograph of FIG. 9.

FIG. 10 illustrates a side or edge view of the 3D vectorcardiograph 12 of FIG. 9. This is another view of the previous display of FIG. 9 showing the 3D vectors 200 on edge. Normal heart vectors 12 in many cases, may lie in a single plane, as evident in FIG. 10. Distortion of the planar characteristic of the normal heart vectors 12 is another indicator of a diseased condition.

Figure 11:
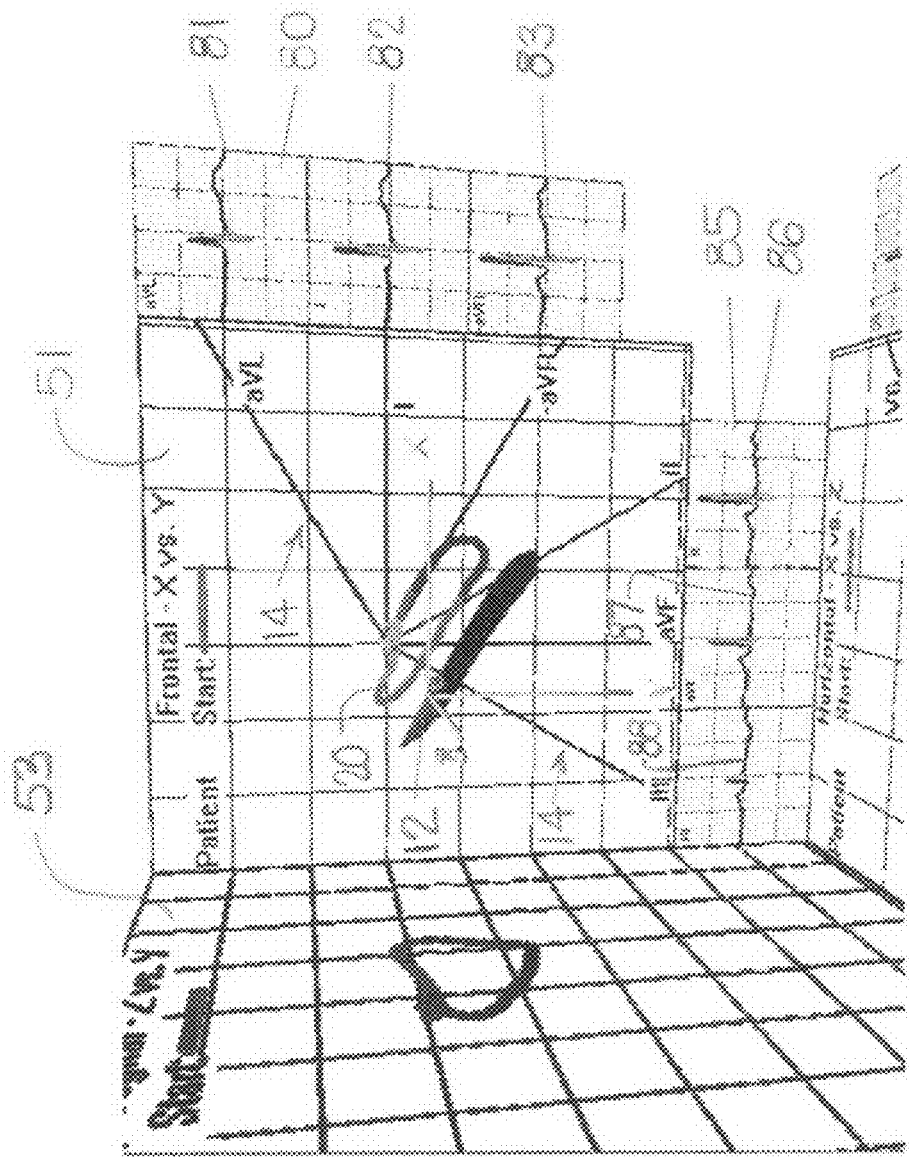
FIG. 11 illustrates a frontal view of a patient having a normal heart with the projections of the vectors onto the lead vectors being displayed.

FIG. 11 illustrates a frontal view of a patient having a normal heart with the projections of the vectors 20 onto the lead vectors 81, 82, 83 and 86, 87, 88 being displayed. The frontal view is obtained by selecting a symbol or marker, e.g., symbol 1090 or .degree. F' on the tool bar 100. The lead vectors 14 for each of the limb leads and the resultant projections 20 of the vectors are clearly shown in a frontal view.

Figure 12:
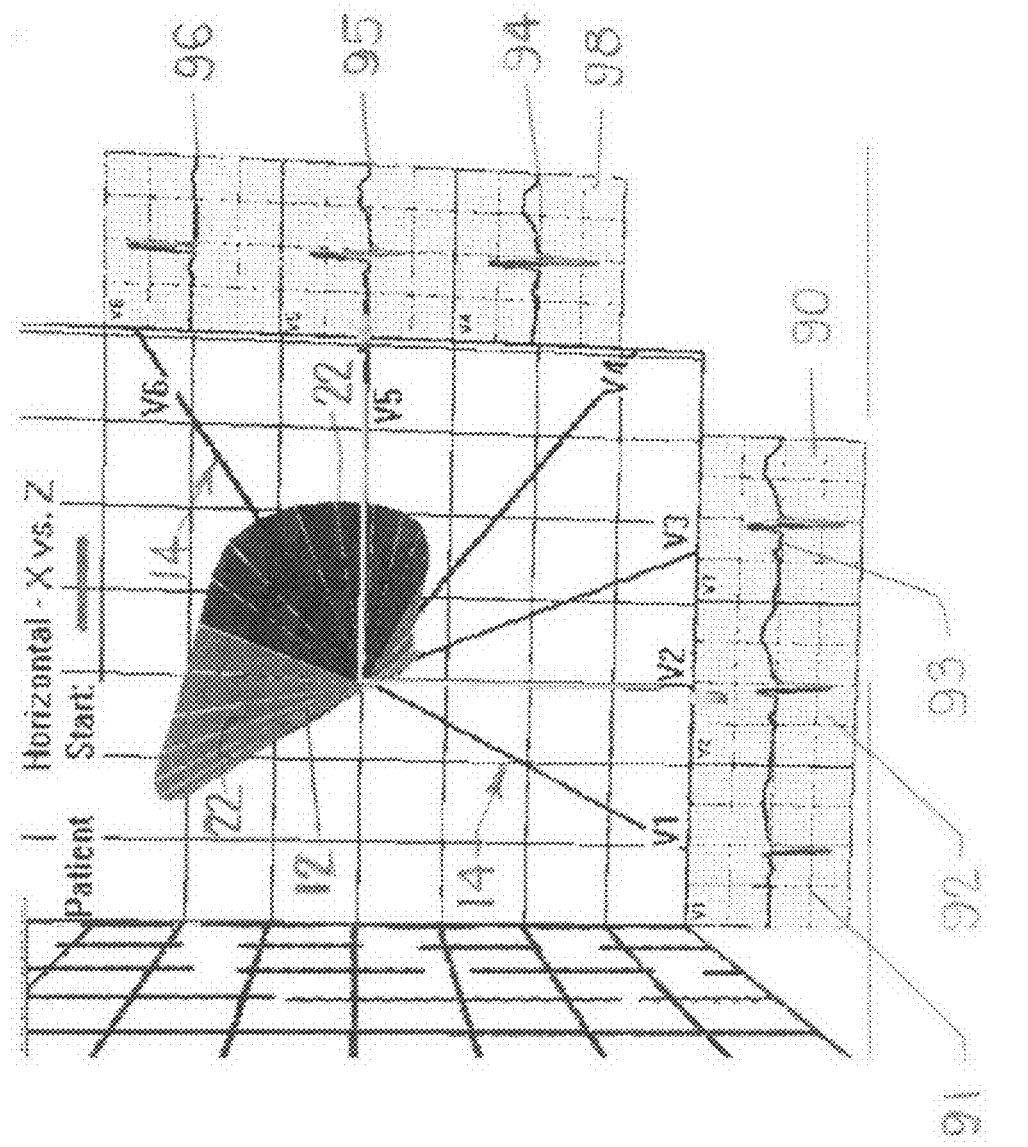
FIG. 12 illustrates a horizontal view of the patient having a normal heart with the projections of the vectors onto the lead vectors being displayed.

FIG. 12 illustrates a horizontal view of the patient having a normal heart with the projections of the vectors 22 onto the lead vectors 91, 92, 93 and 94, 95, 96 being displayed. The Horizontal display is obtained by selecting a symbol or marker, e.g., symbol 1100 or 'H' on the tool bar 100. As in the frontal view, the projections of the vectors 22 onto the lead vectors 14 is displayed.

Figure 13:
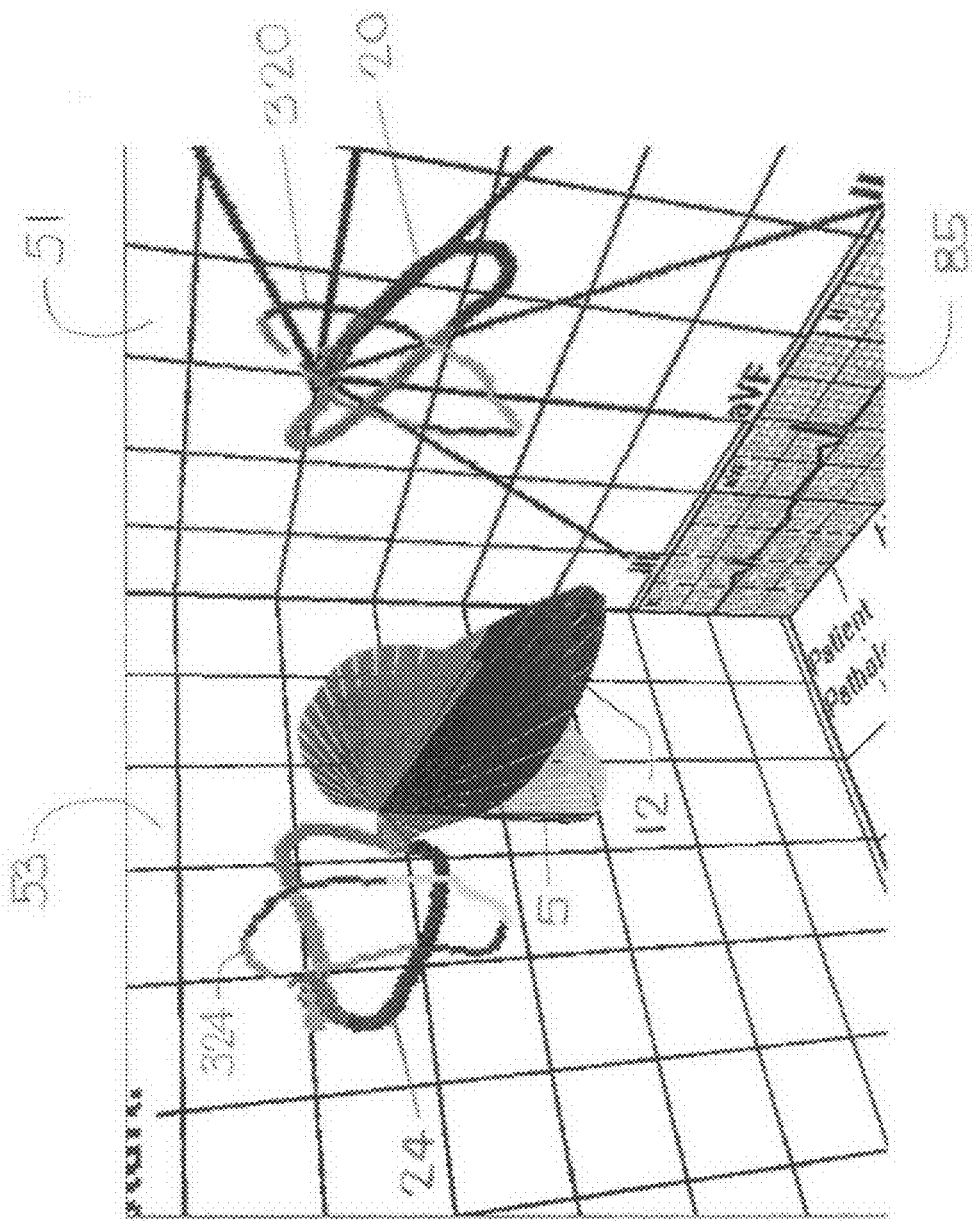
FIG. 13 illustrates the 3D vectorcardiograph of the patient in comparison with a large anterior myocardial infarction (MI)

FIG. 13 illustrates the 3D vectorcardiograph 12 of the normal patient of FIG. 1 in comparison with a large anterior myocardial infarction (MI) 126 (see FIG. 4B). The projections of the MI 126 onto the frontal and sagital planes 51 and 53 are illustrated as 320 and 324, respectively. The dramatic difference in the shape of these curves 320 and 324 as compared to the normal curves 20 and 24, respectively, makes recognition of the diagnosis of a large anterior MI quick and accurate.

The software allows the comparison of a current or prior 3D ECG 12 of a patient with any of the disease types 102 as shown on the tool bar menu 100. Therefore, recognition of the difference in two patterns, such as the normal pattern 12 compared to the large anterior MI 126, through the 3D presentation method of the present disclosure is greatly facilitated.

Figure 14:
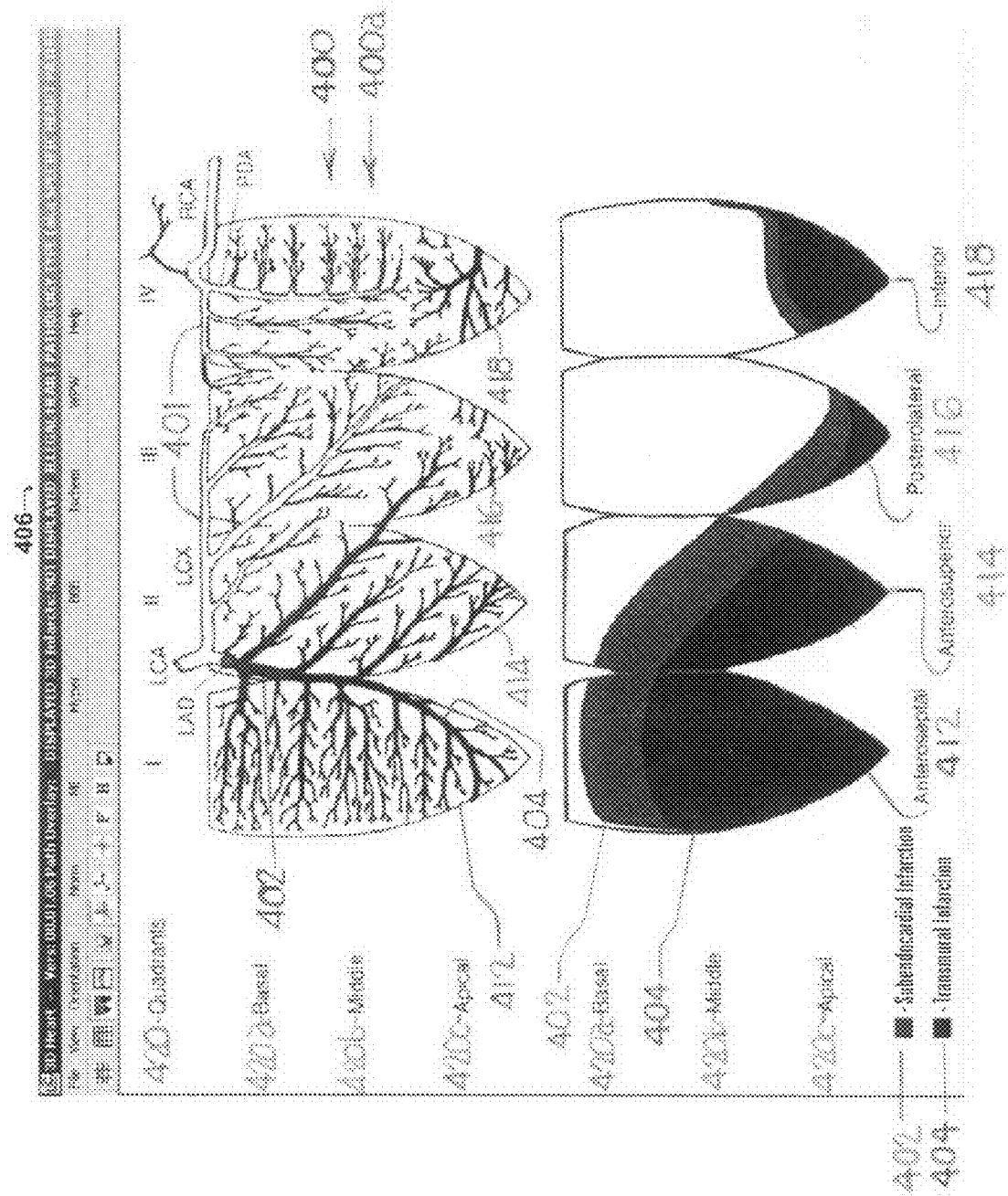
FIG. 14 illustrates a Mercator projection of coronary arteries for two different levels of infarction conditions.

In FIG. 14, a display 406 displays a Mercator projection of the left ventricle of the heart 5. This is advantageous for a user to diagnose what coronary arteries are blocked. In addition, the cardiac conditions 120 for myocardial infarctions (MI) (see FIG. 4B) can be displayed. A Mercator projection 400 of coronary arteries 401 for two different levels of myocardial infarctions is illustrated: a subendocardial infarction 402 shown in blue and a transmural infarction 404 shown in black. By clicking on the symbol or icon 1030 as shown above and in FIG. 4A, a display 406 of the Mercator projection 400 of the coronary arteries 401 is shown for the blockage type indicated. An upper display 400a illustrates the specific locations in the arteries 401 in which the infarctions have occurred. A lower display 400b illustrates the degree of infarction. The Mercator projection displays 400a and 400b are divided into an anteroseptal projection 412, an anterosuperior 414, a posterolateral 416, and an interior 418. The display 406 also provides information regarding quadrants 420: the basal 420a, the middle 420b and the apical 420c. The projections 400a and 400b identify the parts of the myocardium that are damaged when this disease is present. In effect, the display 406 displays an overlay of the picture of coronary arteries 401 as a Mercator projection 400 of a heart.

Figure 15:
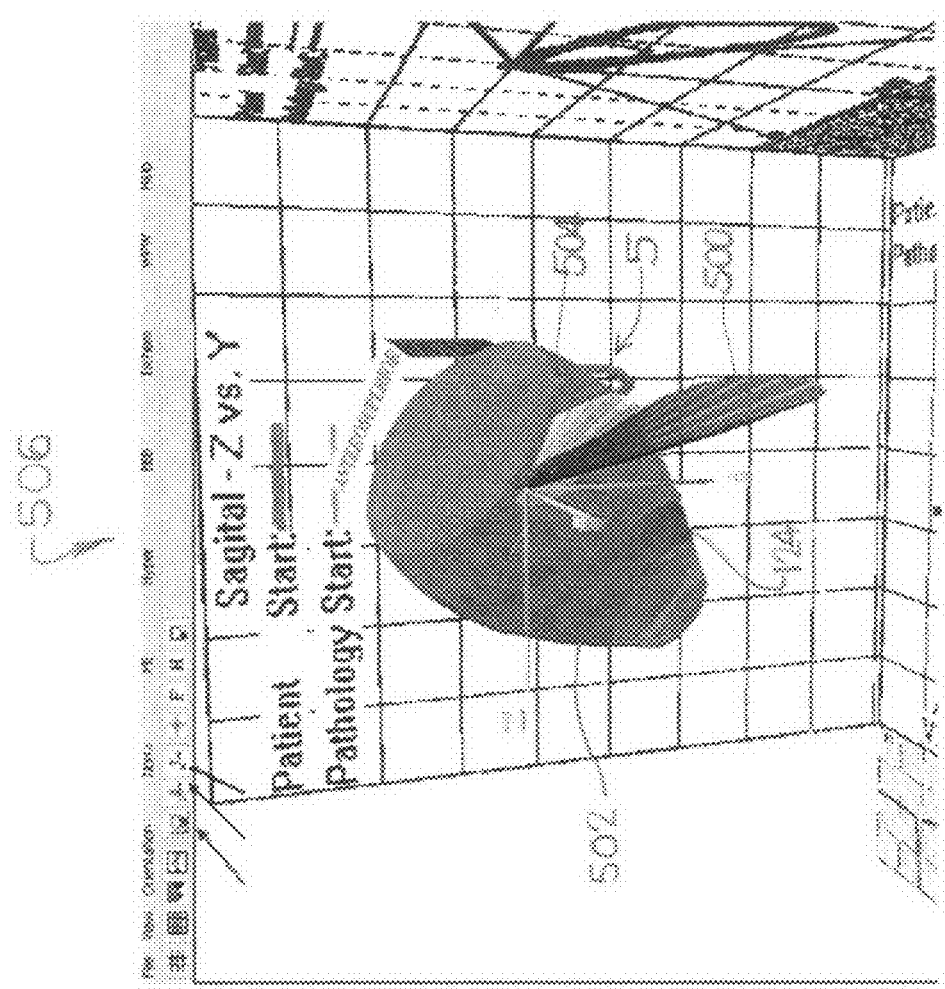
FIG. 15 illustrates a 3D vectorcardiograph of a patient having a medium anterior MI with a dark gray area representing those regions of the heart that are infarcted.

FIG. 15 illustrates a display 506 of a 3D vectorcardiograph 500 of the left ventricle 502 of a patient having a medium anterior MI 124a with a dark gray area 504 representing those regions of the left ventricle 502 that are infarcted. The origin of the vector diagram is positioned at the electrical center of the heart 5. The electrical center is defined as the center and is the origin of the vectorcardiograph 500. The 3D vectors represent the sum of the electrical activity of the myocardium which may be projected from the electrical center. A comparison with the stored version of a medium anterior MI 124 (see FIG. 4B) has been selected as well as the three axes X, Y and Z, and an overlay of the Left Ventricle 502 of the heart. The overlay is activated by selecting the icon 1050 on the display tool bar 400b (see FIG. 4B). The dark gray area 504 of the left ventricle 502 indicates those regions of muscle tissue that are infarcted. The dark regions of the heart 502 that are infarcted do not produce an electrical signal in the anterior direction along the Z axis. As a result, the active sections are mostly posterior and thus make the vectors point primarily in the inferior and posterior direction along the negative Z direction and in the Y direction. In this view, the patient signal looks green and the typical medium anterior MI signal is shown in yellow and green. By rotating the picture, i.e., the 3D vectorcardiograph 500, the total vector diagram can be seen with all the appropriate colors. Thus, recognition of the pattern of the 3D vectors that result is facilitated. This demonstrates quite dramatically the advantages of the 3D vectorcardiogram and its relation to the heart itself.

Figure 16:
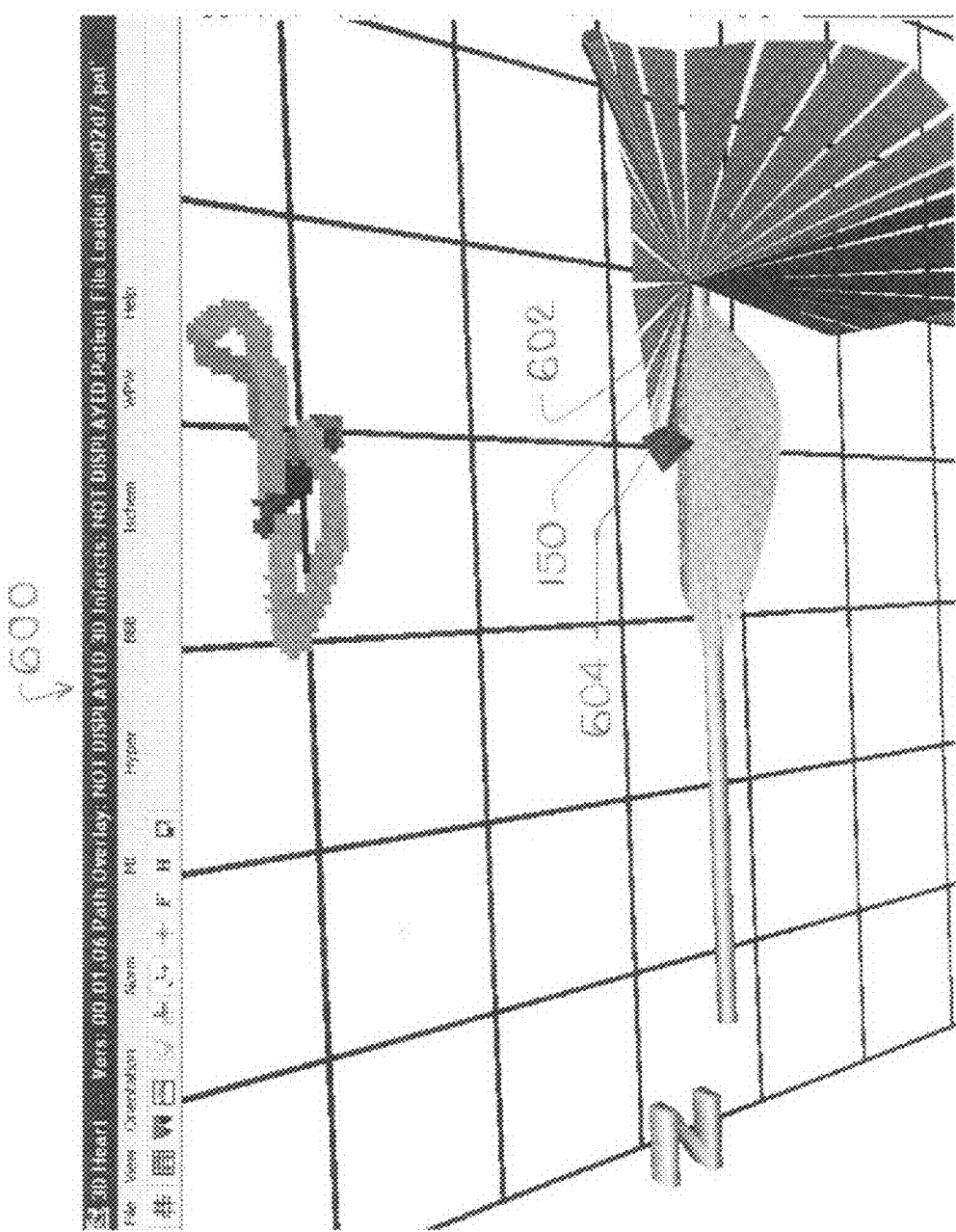
FIG. 16 illustrates a 3D vectorcardiograph of a patient having an ischemic condition represented by a vector.

FIG. 16 illustrates a display 600 of a 3D vectorcardiograph 602 of an ischemic condition 150 (see FIG. 4B) in which the direction of vector 604 clearly indicates the location of the ischemic condition 150 The vector 604 indicating the ischemic condition 150 is drawn at a location in the time sequence that is shortly after the end of the QRS cycle (J-point). The vector 604 is positioned at the J-point plus 60 ms, which is generally recognized to be sensitive to the effects of ischemia. By positioning a vector such as vector 604 at the J-point that is plainly visible, the presence of an ischemic condition may become essentially immediately apparent. The location of the ischemic condition 150 also becomes essentially immediately apparent with respect to the X, Y and Z coordinates, since the vector 604 points toward the area of the heart 5 (see FIG. 1) in which the ischemic condition 150 has occurred. As discussed below with respect to FIG. 19, the area in which the ischemic condition 150 has occurred is found by overlaying a 3D image of the Left Ventricle with the coronary arteries.

Figure 17:
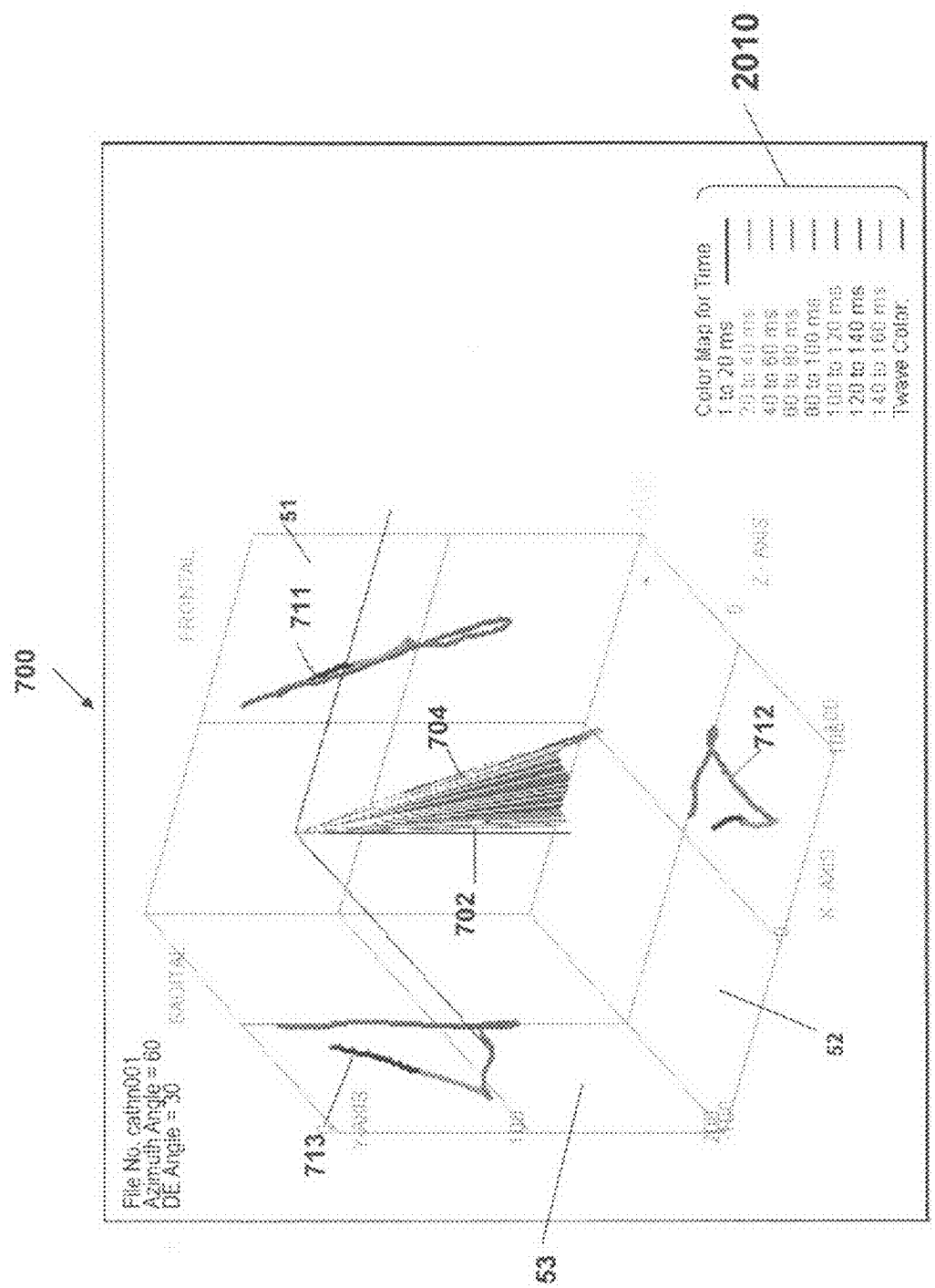
FIG. 17 illustrates a 3D vectorcardiograph of the normal P Wave segment of an ECG signal.

FIG. 17 illustrates a display 700 of a 3D vectorcardiograph 702 of a normal P-wave. A color map 2010, which is scaled at time sequences 2020 of about 20 milliseconds (ms) each is the same as for a QRS complex, as previously described with respect to FIGS. 1, 2, 8-12, and 15-16, since the time scale is about the same. The normal maximum amplitude 704 of the P-wave is between about 100 and about 200 microvolts, for the example as indicated on the X, Y and Z axes defining the frontal, horizontal and sagital planes 51, 52 and 53, respectively. The 3D vectorgraph 702 is projected as first planar projections or vector loops 711, 712 and 713, projected as time sequences, in color-coded form, onto frontal plane 51, horizontal plane 52, and sagital plane 53, respectively. The beginning vectors of vector loops 711, 712 or 713, color coded as black and blue, of the P-wave are associated with the Right Atrium. The latter part of the wave form and latter vectors of vector loops 711, 712 or 713, color coded as purple and green, relate to the Left Atrium. This 3D vectorcardiograph display 700 may form the main display of FIG. 1 and the surrounding panel displays 80, 85, 90, and 98, and the rhythm strip 60, the fiducial points 70, probable patient diagnosis 30, and the statistics of critical measurements 66 may be associated with the properties of the P-wave 3D vectorcardiograph 702.

Figure 18:
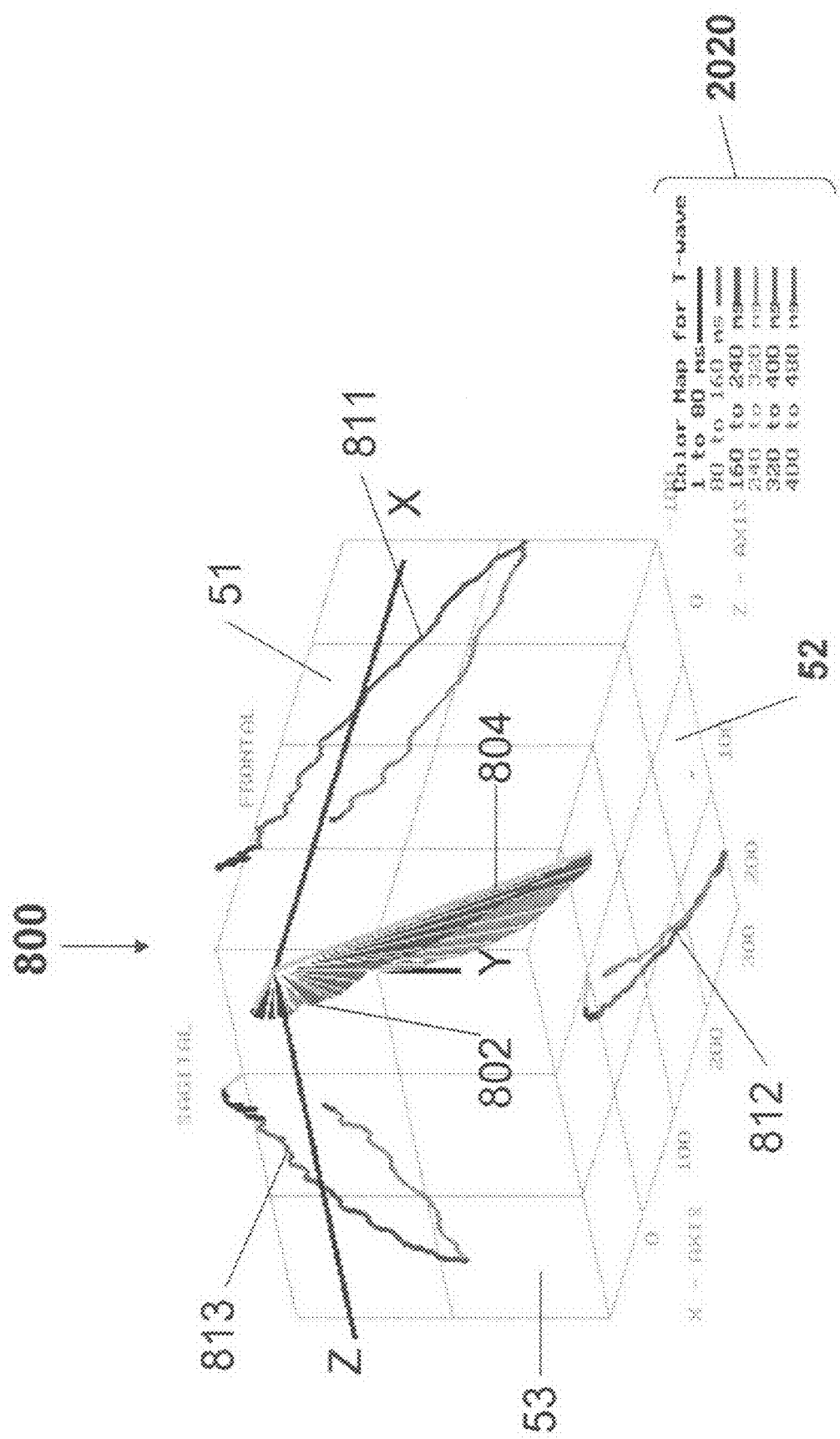
FIG. 18 illustrates a 3D vectorcardiograph of the normal T wave segment of an ECG signal.

FIG. 18 illustrates a display 800 of a 3D vectorcardiograph 802 of a normal T-wave. As compared to color map 2010 with respect to FIG. 17, a color map 2020 for this display is expanded to 80 ms per color, since the time scale is much longer for the T-wave than the QRS. The normal maximum amplitude of the T-wave signal 802 is scaled as necessary to effectively show the signal strength with a value of about 300 microvolts shown for illustrative purposes only, as indicated on the X, Y and Z axes defining the frontal, horizontal and sagital planes 51, 52, and 53, respectively. The 3D vectorgraph 802 is projected as first planar projections or vector loops 811, 812 and 813, projected as time sequences, in color-coded form, onto frontal plane 51, horizontal plane 52, and sagital plane 53, respectively. The normal direction for the T-wave is anterior and inferior, with a fairly narrow displacement about the maximum vector 804. In a similar manner as with respect to the P-wave described above with respect to FIG. 17, the 3D vectorcardiograph display 800 may form the main display of FIG. 1 and the surrounding panel displays 80, 85, 90, and 98, and the rhythm strip 60, the fiducial points 70, probable patient diagnosis 30, and the statistics of critical measurements 66 may be associated with the properties of the T-wave vectorcardiograph 802.

In FIGS. 1, 2, 3, 8, 9, 10, 11, 12, 13, 15, 16, 17, and 18 the cardiographic display 10 operatively communicates with the CPU 82 to implement a diagnostic algorithm 88 (see FIG. 3) to permit a user to selectively and visually convert and display the segment of the patient ECG signal 12 into a color coded projection of a time sequence with planar projections or vector loops 20, 22 and 24 projected as time sequences, in color-coded form, into the three planes: Frontal 51, Horizontal 52 and Sagital 53, respectively, as at least first color-coded projections. The color coded projections 20, 22 and 24 correspond to a magnitude and location of the vectorcardiograph signal 12. The first color-coded sequences 20, 22 and 24 represent a time line duration of the vectorcardiograph signal 12. The first color-coded frontal planar projection or vector loop 20 and 22 in turn may be projected into lead projections as corresponding second color-coded time sequence projections 81, 82, 83 and 86, 87, 88 associated with vector loop 20 and corresponding second color-coded time sequence projections 91, 92, 93 and 94, 95 and 96 associated with vector loop 22.

Figure 19:
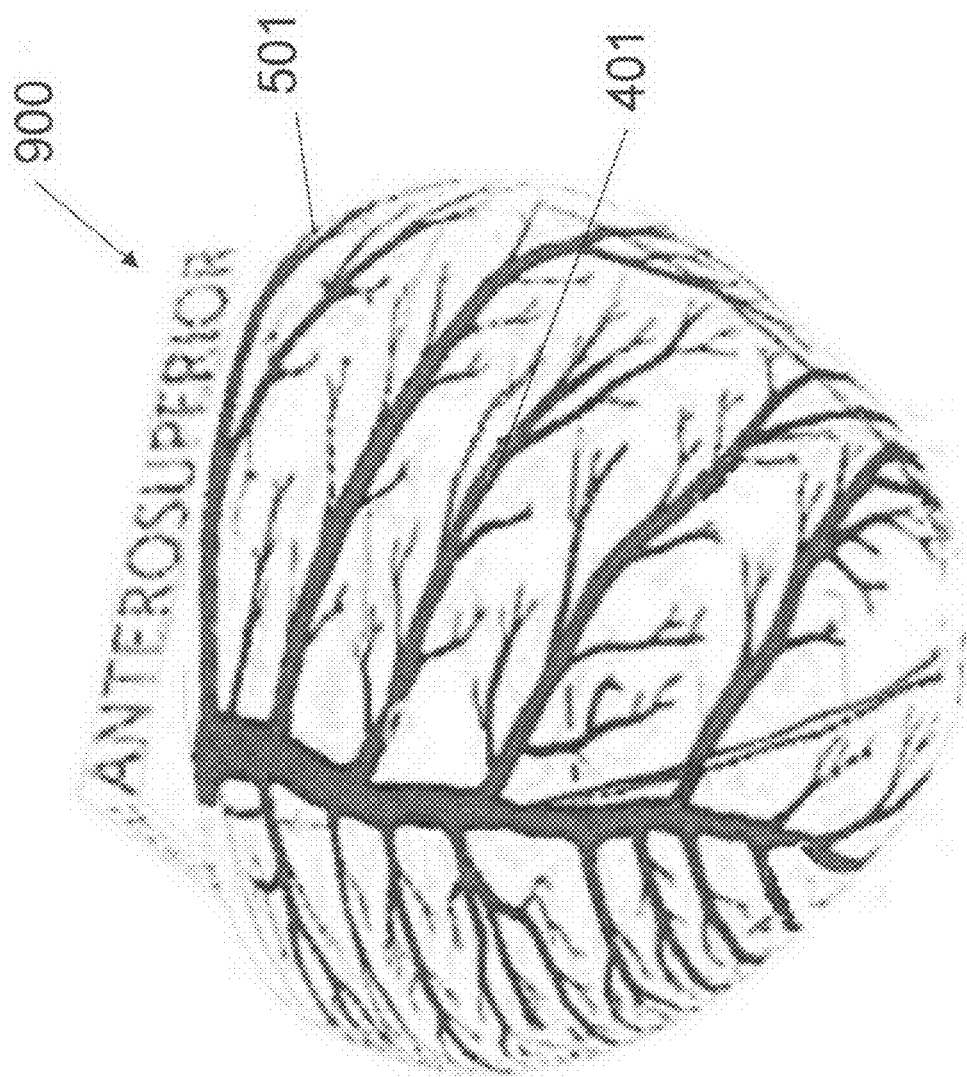
FIG. 19 illustrates a 3D overlay of the coronary arteries of the heart superimposed on a heart.

In conjunction with FIGS. 14 and 15, FIG. 19 illustrates a 3D display 900 of the coronary arteries 401 (see FIG. 14) of a 3D heart 501 as the arteries 401 are associated with the Left Ventricle 501 of the heart 501. The 3D display 900 may be situated at the origin of the X, Y, Z axes (see FIG. 15) and may be made semi-transparent so that the 3D vectorgram or vectorcardiograph of the ECG signal 12 may project through an outer shell or periphery 506 of the heart 501 as illustrated in FIG. 15. Thus, the effects of MI 120 or ischemia 150 (see FIG. 4B) may be associated with the appropriate area of coronary arteries 401 causing the disease state being observed.

As can be appreciated from the foregoing, FIGS. 1-19 present the medical display 10 for analyzing heart signals that includes the cardiographic display 10 which displays an electrocardiograph (ECG) heart signal 12 of a patient having a magnitude and location in vector format 14 within a single three-dimensional (3D) coordinate system, e.g., X, Y, Z, (vectorcardiograph) sampled at incremental time intervals. The display 10 operatively communicates with the CPU 82 that implements a diagnostic algorithm 88 to permit a user to selectively and visually display a comparison 90 of the patient ECG with at least one known display 102 in vector format within a single three-dimensional (3D) coordinate system. The known display(s) consist of a normal cardiac condition 110 (including a patient's prior or current normal condition) or an abnormal or reference cardiac condition that includes at least one of a patient prior or current cardiac condition, a myocardial infarction condition 120, a hypertrophic condition 140, an ischemic condition 150, and a bundle branch block condition 190. The known displays 102 in vector format are stored in the known cardiac conditions database 86, which in turn is stored in the memory 84. (See FIGS. 3 and 4A-4B).

The cardiographic display 10 may operatively communicate with the CPU 82 to allow a user to selectively display critical measurements 66 of at least one of the patient ECG 12, obtained via the patient monitoring 74, and the known display(s) 102 in vector format.

The algorithm 88 may compare the patient ECG critical measurements 66 to the critical measurements stored in the cardiac conditions database 86 and the CPU 82 may operatively communicate with the cardiographic display 10 to visually display the results of the comparison 90 as a normal or abnormal condition. In addition, the cardiographic display 10 may operatively communicate with the CPU 82 to allow a user to selectively display an overlay over the vectorcardiograph patient ECG 12, with the overlay including at least one of a 3D representation of a heart 5, a representation of coronary arteries 400 over a projection of a heart, and a 3D vectorcardiograph 12 of a cardiac condition 102. Also, the segment of patient ECG signal 72 may include at least one of a P-wave interval, PR interval, QRS interval, QT interval and T-wave interval (see FIG. 6).

Referring again to FIGS. 1-19, it can be appreciated also that the present disclosure relates to a method for analyzing heart signals, which includes the step of implementing the algorithm 88 to permit a user to selectively and visually display a comparison of the electrocardiograph (ECG) heart signal 12 of a patient having a magnitude and location in vector format within a single three-dimensional (3D) coordinate system (vectorcardiograph) sampled at incremental time intervals with at least one known display 102 in vector format within a single three-dimensional (3D) coordinate system. The known display(s) consist of a normal cardiac condition 110 (including a patient's prior or current normal condition) or an abnormal or reference cardiac condition that includes at least one of a patient prior or current cardiac condition, a myocardial infarction condition 120, a hypertrophic condition 140, an ischemic condition 150, and a bundle branch block condition 190. As previously indicated, the known displays 102 in vector format are stored in the known cardiac conditions database 86, which in turn is stored in the memory 84. (See FIGS. 3 and 4A-4B).

The step of implementing the algorithm 88 may further include implementing the algorithm to allow the user to selectively display the critical measurements 66 of at least one of the segment of patient ECG 12 signal and the known display in vector format 102. The step of implementing the algorithm further may also include implementing the algorithm 88 to allow a user to compare the patient ECG critical measurements 66 to critical measurements 86 stored in a database and to operatively communicate with the cardiographic display 10 to visually display the results as a normal or abnormal condition. The step of implementing the algorithm may further include implementing the algorithm 88 to allow a user to selectively display an overlay over the vectorcardiograph patient ECG 12. The overlay includes at least one of a 3D representation of a heart 5, a representation of coronary arteries 400 over a projection of a heart, and a 3D vectorcardiograph 12 of a cardiac condition 102. The segment of the patient ECG signal 12 may include at least one of a P-wave interval, PR interval, QRS interval, QT interval and T-wave interval (72 in FIG. 6).

The present disclosure relates also to a method of displaying the electrocardiograph (ECG) heart signal 12 having a magnitude and location in vector format within a single three-dimensional (3D) coordinate system (e.g., X Y Z) sampled at incremental time intervals, which includes implementing the steps of displaying the cardiac conditions 102 and separating the cardiac conditions 102 into recognizable patterns of 3D vectors 14.

Referring to FIGS. 1-3, the method may include displaying the critical measurements 66 of at least one of the recognizable patterns of 3D vectors 14 and comparing the display of critical measurements 66 to statistical information for at least one of the cardiac conditions 102. The cardiac condition may be a normal condition 110 or an abnormality such as, but not limited to, MI 120, hypertrophy 140, ischemia 150, or BBB 190 and their sub-categories.

As illustrated in FIGS. 7-12, the method may include the step of displaying the heart signal 12 in X, Y and Z vector signals 14 and the resultant magnitude of the signal $Mag._{vd} = \{\sqrt{(x^2 + y^2 + z^2)}\}$, as previously described. Alternatively, other 3D coordinate systems such as cylindrical coordinates may be implemented to perform the method. The embodiments are not limited in this context. The method may include utilizing the X, Y and Z vector signals 14 and the resultant magnitude of the signal $Mag._{vd}$ to illustrate an estimate of at least the P-wave interval, or the PR interval, or the QRS interval, or the QT interval or the T-wave interval. FIGS. 7-12 also illustrate that the method may include displaying an overlay of a 3D picture of a heart 5 over the 3D vectorcardiograph 12.

Alternatively, or in addition thereto, as also illustrated in FIG. 14, the method may include the step of displaying an overlay of a 3D ECG of a cardiac condition, e.g., MI 126, over the 3D ECG of the patient 12. As illustrated in, and described above with respect to, FIGS. 15 and 19, the method may include displaying an overlay of a picture of coronary arteries 401 over a 3D projection of a heart 501. As can be appreciated, the present disclosure relates to a 3D cardiographic display and method based on software tools to enhance diagnostic presentation of ECG data. The cardiographic display and the method of presentation separate the various heart abnormalities into easily recognizable patterns of 3D vectors. The software provides a comprehensive "menu" of diagnostic and treatment decision support tools. The support tools may include:

Comparison of the patient 3D display with known patterns for a selected abnormality.

Previous ECGs from that patient and their patterns.

Critical measurements of the 3D pattern and comparison with statistical information for known abnormalities providing Z scores.

A rhythm strip to show any abnormalities in this venue.

The presentation of one heart cycle showing X, Y, and Z signals and their resultant magnitude for the best estimates of P-wave Duration, PR interval, QRS duration, and QT interval.

The ability to overlay the 3D picture of the heart on top of the 3D vectorcardiogram to identify areas of disease such as MI and ischemia.

The ability to overlay the picture of the coronary arteries on top of the heart to locate the region of ischemia in 3D or as a Mercator projection.

With respect to locating a region of ischemia in 3D or as a Mercator projection, as mentioned herein above, since the axis of the heart is offset from the vertical and horizontal positions of the body, i.e. the vertical and horizontal axes of the torso, and the vector location of the ischemic vector is in relationship to the body coordinates, it is difficult for the attending physician to mentally visualize the precise location of the ischemic region from the ECG measurements, which are taken with respect to the body positions. The mental visualization is currently necessary for the attending physician to determine the precise location of the ischemic region.

As discussed above, the axis of the heart is offset from the vertical and horizontal positions of the body, i.e. the vertical and horizontal axes of the torso, and the vector location of the ischemic vector is in relationship to the body coordinates.

Figure 20A:
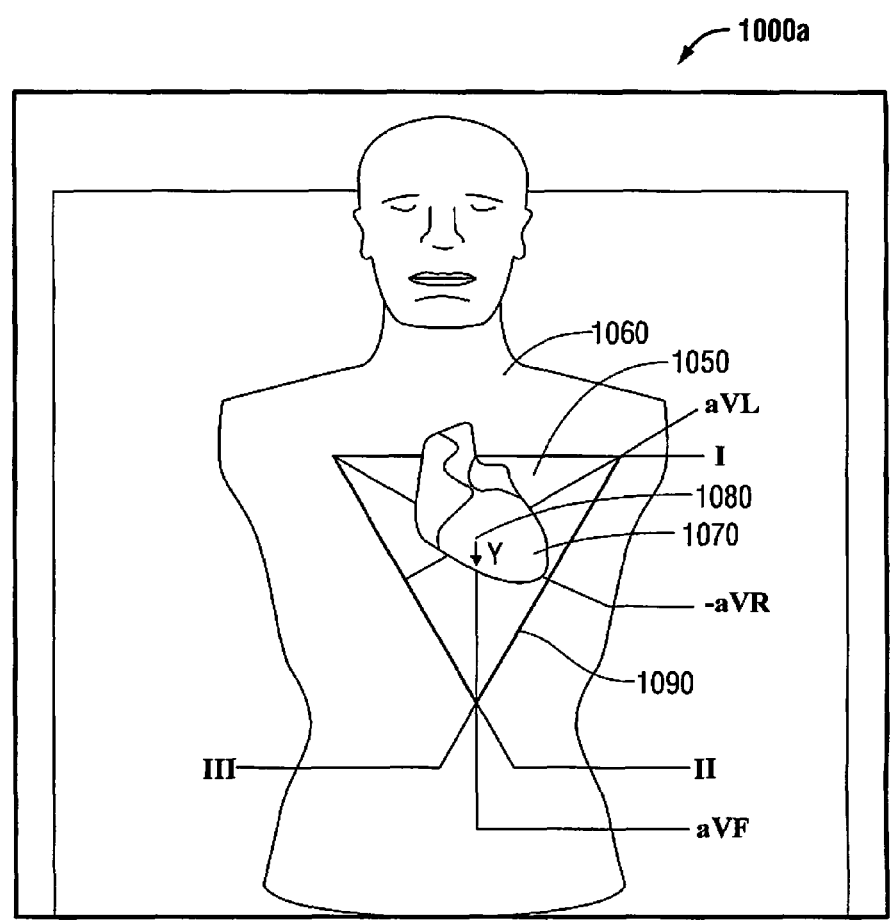
FIG. 20A illustrates six leads of a 12-lead electrocardiogram with respect to a vertical plane in the torso that passes through the electrical center of the heart.
Figure 20B:
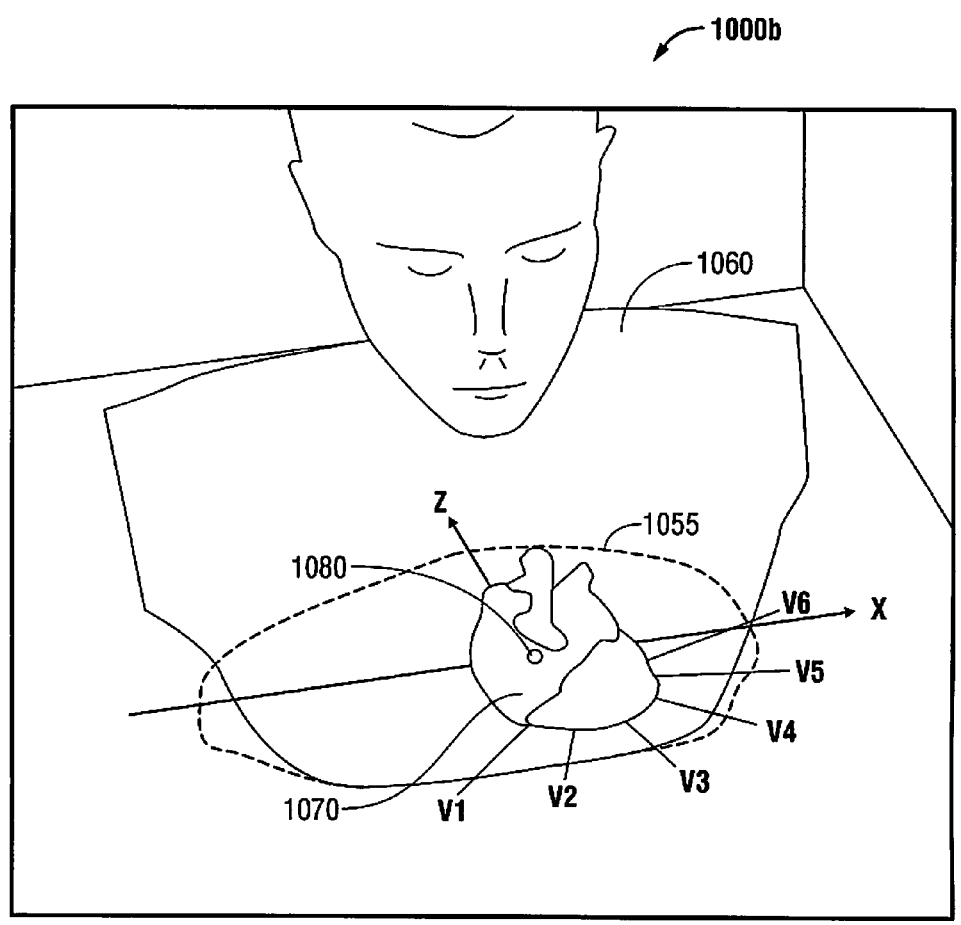
FIG. 20B illustrates the remaining six leads of the 12-lead electrocardiogram of FIG. 20A with respect to a horizontal plane in the torso that passes through the electrical center of the heart and intersects the vertical plane of FIG. 20A.

This is illustrated in FIGS. 20A and 20B. In FIG. 20A, display 1000a shows six Limb leads of a 12-lead electrocardiogram, i.e., leads aVL, I, -aVR, II, aVF and III, with respect to a vertical plane 1050 in the torso 1060 that passes through the electrical center 1080 of the heart 1070. The vertical plane 1050 is defined by the X and Y axes having the electrical center 1080 as the origin.

Using only three leads in the frontal plane 1050, e.g., leads I, II, III, an Einthoven triangle 1090 is constructed to provide a triaxial reference system for viewing the cardiac electrical activity of the heart 1070. The additional leads, aVL, -aVR and aVF are derived from these leads and represent directions that are 30 degrees offset from the basic I, II, and III leads.

In FIG. 20B, display 1000b shows the remaining six precordial leads of a 12-lead electrocardiogram, i.e., leads V1, V2, V3, V4, V5 and V6, with respect to a horizontal plane 1055 in the torso 1060 that similarly passes through the electrical center 1080 of the heart 1070 and intersects the vertical plane 1050 (shown in FIG. 20A). The horizontal plane 1055 is defined by the X and Z axes having the electrical center 1080 as the origin. The origin of the vertical Y axis in FIG. 20A coincides with the origin of the X and Z axes at the electrical center 1080.

Figure 20C:
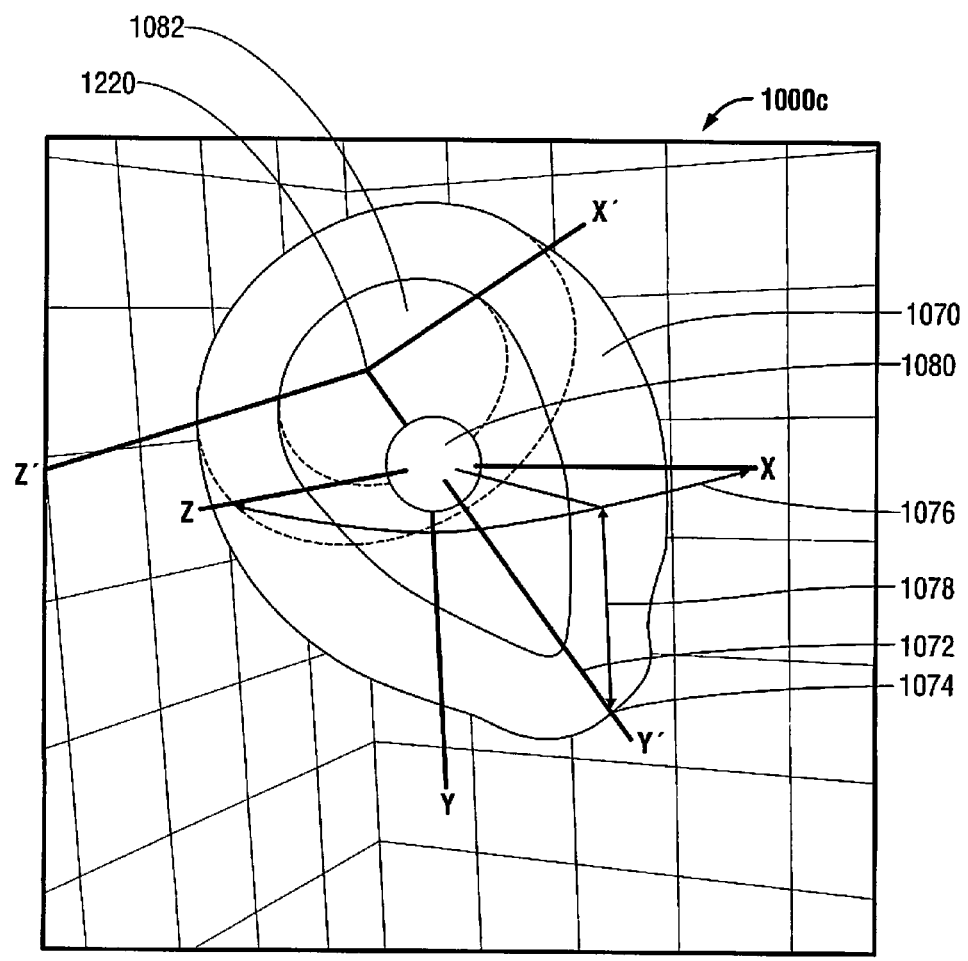
FIG. 20C illustrates the heart in the heart's real position offset with respect to three dimensional coordinates of the torso.

In FIG. 20C, display 1000c shows the orientation of the heart 1070 in the heart's position with respect to the XYZ coordinate axes of the torso 1060 illustrated in FIGS. 20A and 20B where the origin of the XYZ coordinate axes is the electrical center 1080 of the heart 1070. The left ventricle of the heart 1070 generally defines a vertical axis 1072 through the apex 1074. The heart axis 1072 is oriented at an azimuth angle 1076 which has been determined statistically to have on average an angle of about 46° from the X-axis in the X–Z horizontal plane. In addition, the heart axis 1072 is oriented at an elevation angle 1078 which has been determined statistically on average to be about 40° in the Y direction below the X–Z horizontal plane.

Figure 20D:
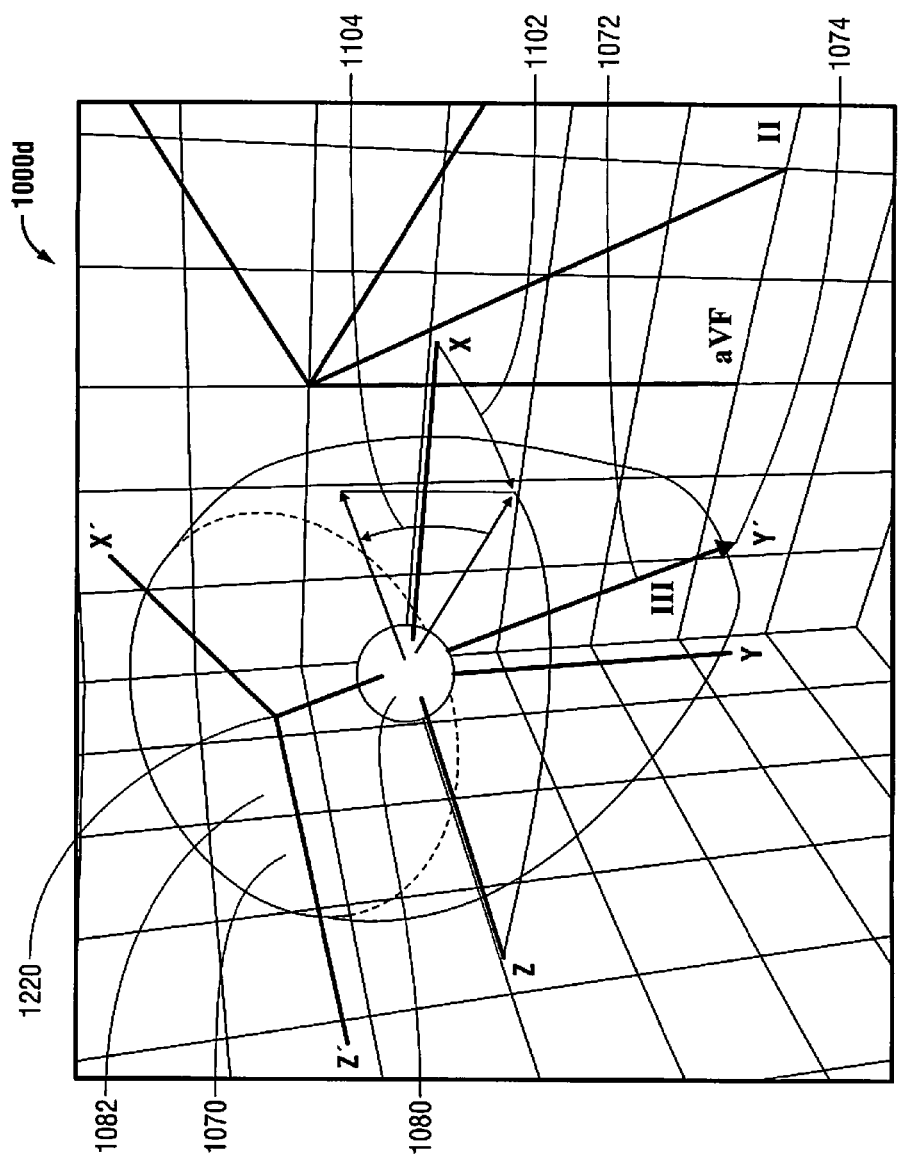
FIG. 20D illustrates the heart in the heart's real position and an ECG signal positioned with respect to the leads of the 12-lead electrocardiogram of FIGS. 20A and 20B.

In FIG. 20D, display 1000d also illustrates the heart 1070 in the heart's position with respect to the XYZ coordinate axes of the torso 1060 illustrated in FIGS. 20A and 20B where the origin of the XYZ coordinate axes is the electrical center 1080 of the heart 1070. The vertical axis 1072 is again illustrated passing through the apex 1074. The ECG data has been processed to identify a vector most pertinent to an ischemic event with respect to the three dimensional coordinate axes XYZ with respect to the torso 1060 illustrated in FIGS. 20A and 20B. More particularly, the vector most pertinent to an ischemic event is ST vector 1100. The ST vector 1100 originates from the electrical center 1080 and, in the example illustrated herein, points to a region on the surface of the heart 1070, as seen in FIG. 20D. The ST vector 1100 also forms an azimuth angle 1102 in the XZ plane and an elevation angle 1104 in the vertical plane that passes through the ST vector and intersects the XZ plane to provide the XZ vector direction as seen in FIG. 20D. The Azimuth angle 1102 and the Elevation angle 1104 are measured by the necessary operations on the ECG data.

Thus, the axis 1072 of the Left Ventricle (LV) of the heart 1070 is normally at an angle pointing anteriorly and inferiorly within certain limits. As indicated above, it is at an angle of 40 degrees down in the frontal plane and at an angle of 46 degrees from the horizontal axis of the body from right to left in the horizontal plane in an anterior direction. These angles may be varied if it is found that certain population groups are more likely to have a different statistical result due to age, sex or physical size. The LV is the primary origin of the electrical vector due to ischemia and the Mercator projection of the coronary arteries are in reference to the sections of the LV.

As can be appreciated from the foregoing discussion of FIGS. 20A-20D, the ST vector 1100 occurs at azimuth angle 1102 and elevation angle 1104 that are different from azimuth angle 1076 and elevation angle 1078 of the heart axis 1072.

Therefore, it is difficult for the attending physician to mentally visualize the precise location of the ischemic region from the ECG measurements, which are taken with respect to the body positions and coordinates X, Y, Z. However, the mental visualization is currently necessary for the attending physician to determine the precise location.

FIGS. 21-26 illustrate various pictorial images projected on a medical display for implementing a method of locating a particular area in the heart where an ischemic event has occurred according to one embodiment of the present disclosure. The method includes mapping the plurality of lead signals of the ECG that correspond to the coordinates of the ECG on the torso, as described above with respect to FIGS. 20A-20D, to three dimensional coordinates with respect to the torso. For the purposes of illustration and discussion herein, reference to the torso is to the human torso. However, those skilled in the art will recognize that the methods and displays disclosed herein may also be applied to the torso of an animal.

Figure 21:
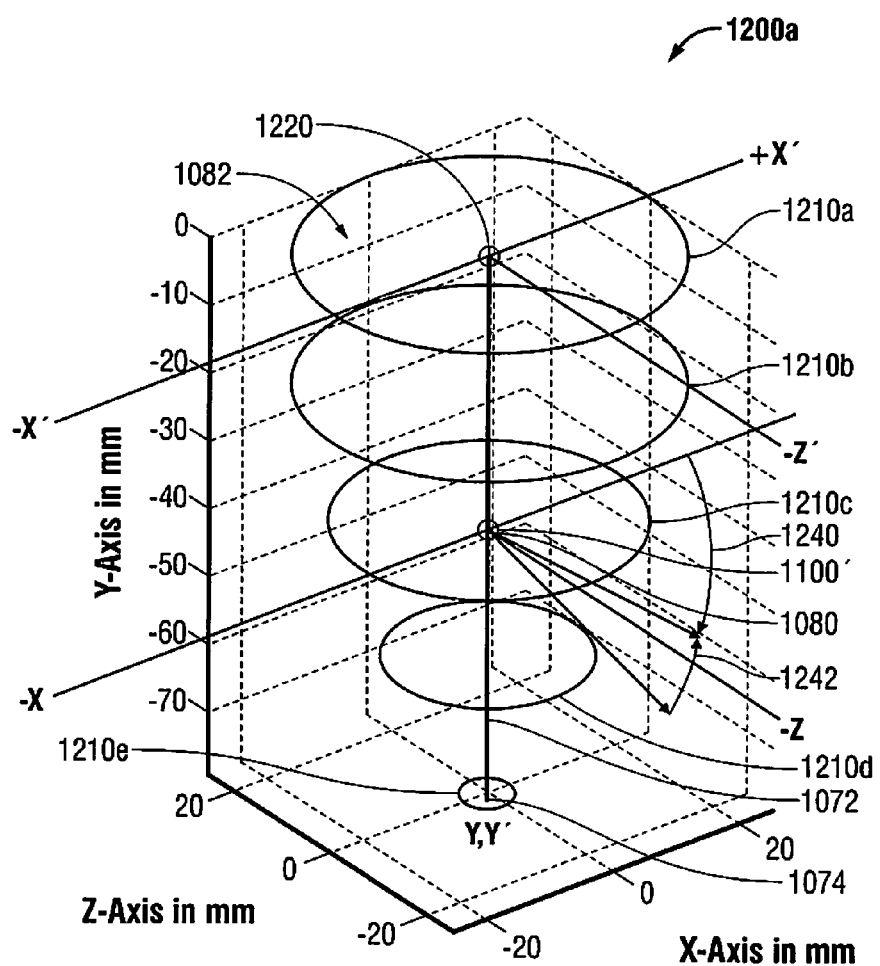
FIG. 21 illustrates one embodiment according to the present disclosure of cross-section representations of the left ventricle of the heart and an st-vector in three dimensions as illustrated in FIG. 20D.

FIG. 21 illustrates a display 1200a of the Left Ventricle of the heart 1070. The left ventricle of the heart 1070 is represented by parallel circular cross-sections 1210a through 1210e in three dimensions X', Y', Z'. In this display 1200, the origin of the X', Y', Z' coordinate axes does not originate at the electrical center of the heart 1070. Rather, referring also to FIGS. 20C and 20D, the origin 1220 and the coordinate axes X'Y'Z' extending along the base 1082 of the heart 1070 and the vertical Y' axis 1072 of the heart 1070 have been shifted so that the origin 1220 of the base 1082 of the left ventricle representing the heart 1070 coincides with the direction of the vertical torso coordinate axis Y. The Y'-axis passes through the origin 1220 and also the electrical center 1080 of the heart 1070. The dimensions of the heart 1070 are measured vertically downward from the origin 1220 in the −Y' direction from 0 millimeters (mm) in the X'Z' plane at the base of the left ventricle 1082 to −80 mm at the apex 1074. This represents the average dimensions of a normal heart. The dimensions of the heart 1070 are measured laterally in the X'Z' plane from 0 mm to ±20 mm in the X' and Z' directions from the vertical axis Y'.

FIG. 21 illustrates a solution to the quandary of the attending physician having to mentally visualize the precise location of the ischemic region from the ECG measurements. More particularly, FIG. 21 illustrates a method according to an embodiment of the present disclosure which may be implemented by translating the ST vector 1100 by vector rotation to the axis 1072 of the heart 1070, using the average measurements for the azimuth angle 1076 of the left ventricle in the torso (not shown). The electrical center 1080 of the heart 1070 is used as the origin of the ST vector 1100 and the location of the ST vector 1100 on the surface of the left ventricle is computed by vector analysis. The vertical heart axis 1072 has been rotated so that the heart 1070 assumes an imaginary position such that the vertical axis 1072 coincides with the body coordinates X, Y, Z described above with respect to FIGS. 20A-20D.

In this position, the heart axis 1072 no longer has an azimuth angle and an elevation angle with respect to the body coordinates X, Y, Z. Rather, there are now a single transformed azimuth angle 1240 and a single transformed elevation angle 1242 that are now associated solely with the ST vector 1100.

The ST vector 1100 having an origin at the electrical center 1080 of the heart 1070 now can be located as coinciding with the electrical center 1080 which is generally recognized as about the mid point of the long or vertical axis −Y' of the heart 1070, i.e., at about −40 mm. This can be seen by the dashed line projection 1100' of the tail of the ST vector 1100 that intersects with the −Y' axis at −40 mm. After translation, the long axis is the Y' axis and, in the example shown, the ischemic or ST vector 1100 has its origin on the Y' axis at a point half way between the extremes of the LV when plotted in this way.

Thus, the problem of locating the ischemic vector, e.g., ST vector 1100, has been simplified. The rotation of the heart 1070 to an imaginary position may be performed by a three dimensional matrix transform which may also be used to rotate the ischemic vector or ST vector 1100.

The single transformed azimuth angle 1240 of the ischemic vector 1100 is now in the X–Z plane. Similarly, the single transformed elevation angle 1242 is now in X–Y plane. Both the azimuth angle 1240 and the elevation angle 1242 can easily be located on a Mercator projection, since all of the horizontal sections are spread over a 360 degree span. This is a circle of the sections of the heart spread out in the Mercator projection. Since the Mercator diagram is split into 4 equal quadrants each quadrant must be 90 degrees in width.

Figure 22:
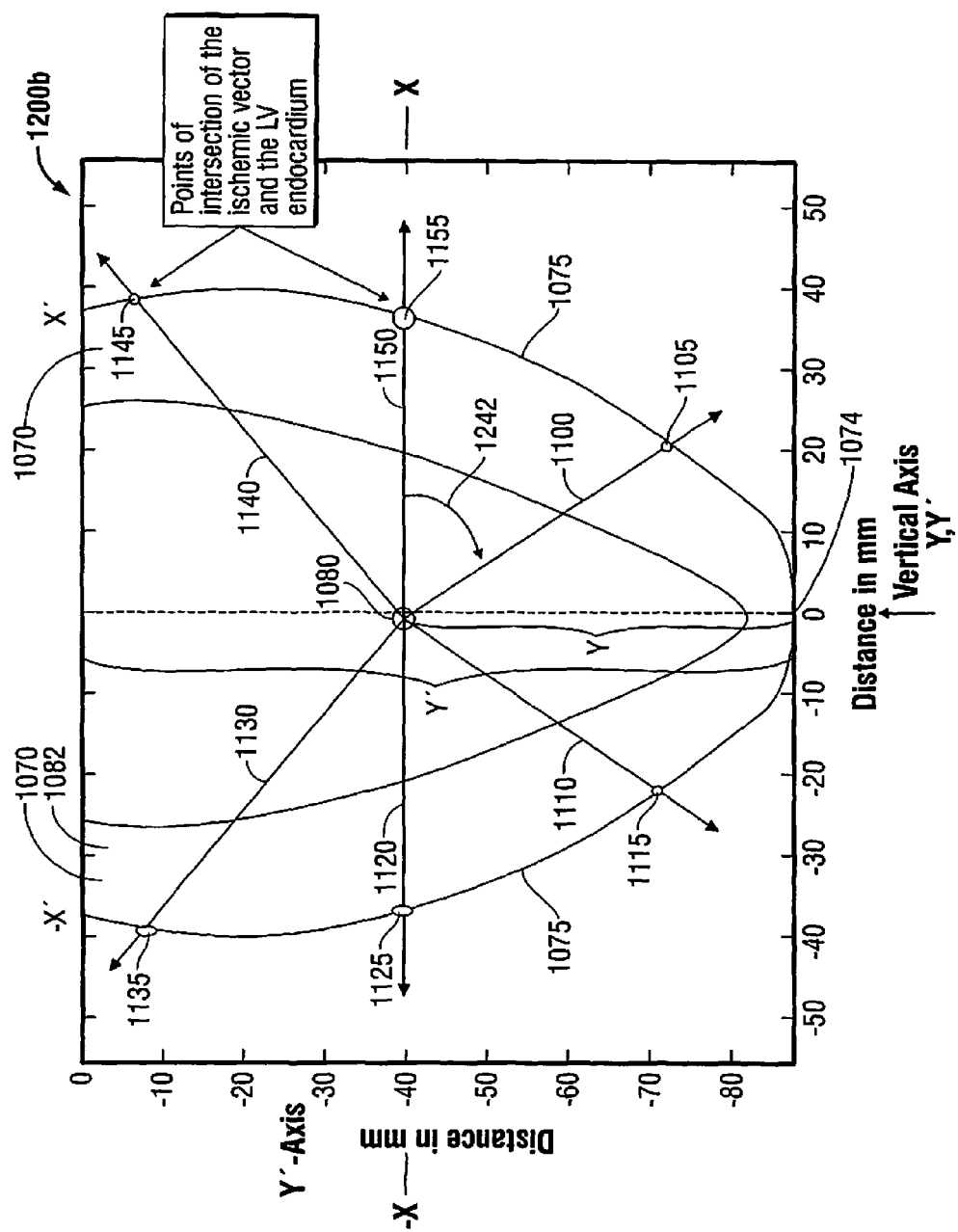
FIG. 22 illustrates one embodiment according to the present disclosure of a vertical cross-section of the left ventricle of the heart with respect to the electrical center of the heart and showing multiple vectors representing the direction of possible ischemic events.

In FIG. 22, display 1200b illustrates a simplified vertical cross section of a typical heart, e.g., heart 1070 of FIGS. 20A-20D and 21, represented by the Left Ventricle extending from the base 1082 to the apex 1074, and also illustrates how this method of rotating the heart and the ischemic vector of concern makes it much easier to find the point on the heart that represents the maximum activity due to the ischemia being experienced by the patient. The single transformed azimuth angle 1240 of the ST vector 1100 in the horizontal X-Z plane is determined from the X and Z components of this vector and this can be converted to an angle by finding the arctangent of these components, as follows:

$$\text{Azimuth Angle} = \arctan(Z, X)$$

Along the vertical axis of the diagram in display 400, the elevation angle of the ischemic vector will determine the intersection of the outer boundary of the heart, e.g., the epicardium 1075, and the location in the Y dimension. A vertical angle of intersection, e.g., the elevation angle 1242 of FIG. 21, can be derived for a given ischemic vector, say ST vector 1100, which along with the horizontal angle, e.g., azimuth angle 1240 of FIG. 21, determines a unique location 1105 for the ischemic event.

The unique location 1105 can be illustrated in a Mercator projection as discussed below with respect to FIGS. 23-25 and can be illustrated in a polar plot of the heart as discussed below with respect to FIG. 26. This can then be used to identify the location of the ischemia and provide information that the physician can use to improve treatment of the heart problem.

At the electrical center 1080 of the heart 1070, a number of other vectors 1110, 1120, 1130, 1140 and 1150 and unique locations 1115, 1125, 1135, 1145 and 1155, respectively, are shown to represent other possible directions of ischemic vectors that might occur. Since the LV is a body of revolution about the vertical axis Y', shown from 0, 0 to 0, −80 mm, the exemplary direction of the vectors 1110, 1120, 1130, 1140, 1150 may occur at any of the cross sections, e.g., 1210a, 1210b, 1210c, 1210d, 1210e in FIG. 21, in the horizontal X'Z' plane. Thus, the vertical angle has a unique relationship to the point of intersection with the surface, e.g., epicardium 1075, of the heart 1070, in terms of the level along the Y' axis and is measured as a distance from the base 1082 of the LV (heart 1070) as shown in the vertical Y' axis. The unique locations 1115, 1125, 1135, 1145 and 1155 are also points of intersection of their respective vectors 1110, 1120, 1130, 1140, 1150.

FIGS. 23-26 further illustrate the process for implementing the method of locating a particular area in the heart where an ischemic event has occurred according to one embodiment of the present disclosure.

Figure 23:
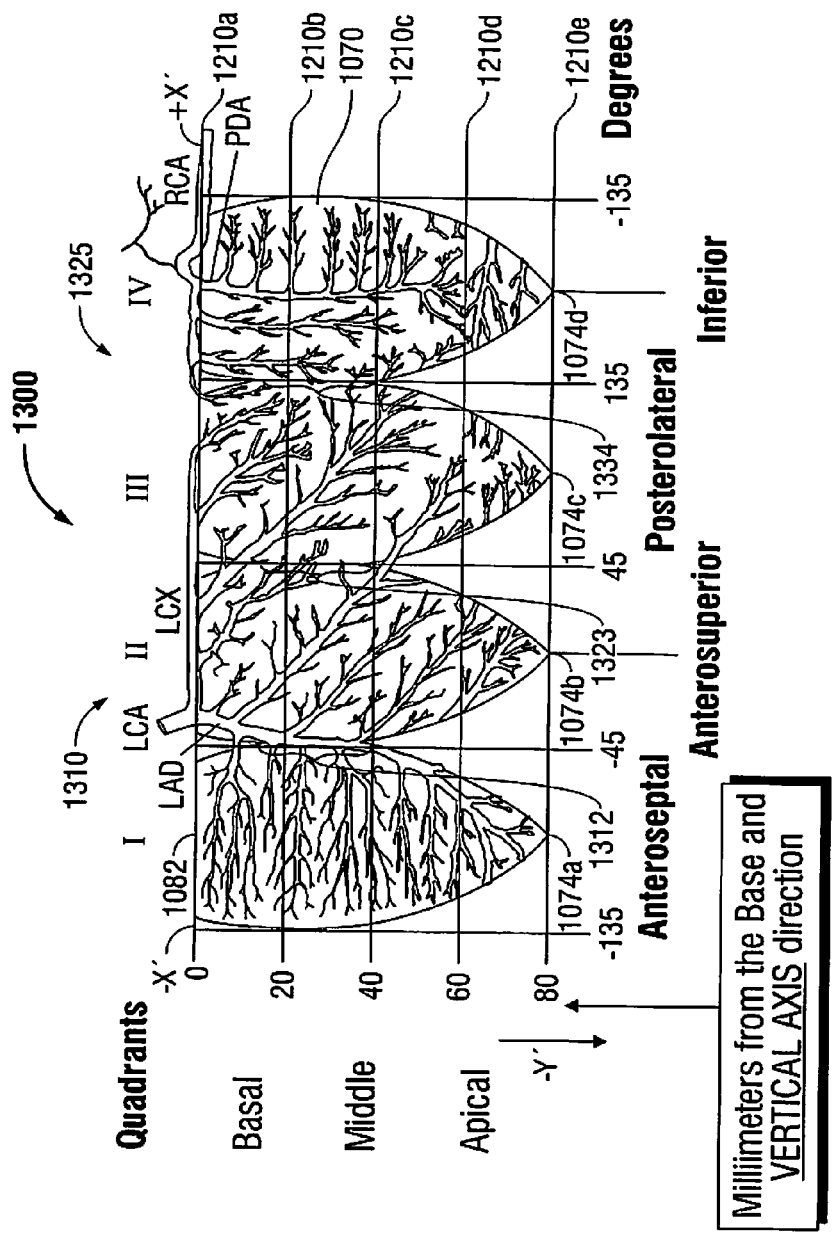
FIG. 23 illustrates one embodiment according to the present disclosure of a 3D Mercator display of the left ventricle of the heart and the coronary arteries and the distance and orientation of a cardiac reference axis.
Figure 24:
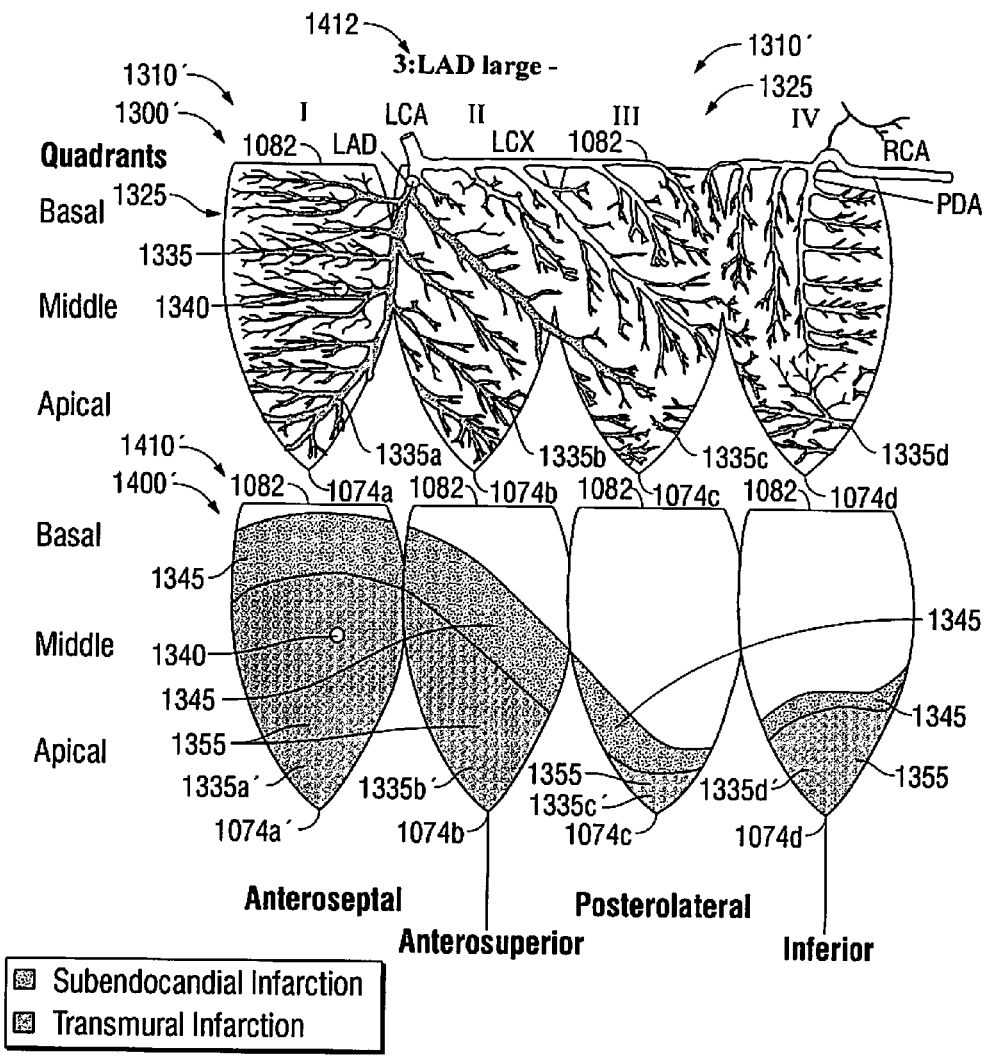
FIG. 24 illustrates one embodiment according to the present disclosure of a representation of the left ventricle of the heart in three dimensions showing the location of a coronary blockage and the centroid of an ischemic region.

In FIG. 23, display 1300 shows a Mercator projection 1310 of the heart 1070 (see FIG. 24 and coronary arteries 1325 for the Left Ventricle). As previously described with respect to FIGS. 20C, 20D, 21 and 22, the LV representing the heart 1070 is a body of revolution about the vertical heart axis or Y' axis. As illustrated in FIG. 21, each parallel cross-section in the X'-Z' plane is a circle, e.g., cross-sections 1210a, 1210b, 1210c, 1210d, 1210e, and are located in the display 1300 in FIG. 23 as horizontal lines a certain number of millimeters from the base 1082 of the left ventricle (representing the heart 1070) at the 0 mm position of the Y' axis at top of the Mercator projection 1310. The circular cross-sections 1210a, 1210b, 1210c, 1210d, 1210e are located in relationship to their degrees around their respective circle and generally with respect to the Basal, Middle and Apical regions of the left ventricle representing the heart 1070. The degrees for the maximum diameter circles which occur at the widest level of the Mercator diagram, about −20 mm are shown for the points of intersection of the four quadrants: Quadrant I. Anteroseptal from −135 degrees to −45 degrees; Quadrant II. Anterosuperior from −45 degrees to 45 degrees; Quadrant III. Posterolateral from 45 degrees to 135 degrees; Quadrant IV. Inferior from 135 degrees through 180 degrees back to −135 degrees. At other levels the boundaries are less so that the 90 degree spread must be reduced to exactly match the dimensions at that level. Quadrants I and II intersect at intersection 1312. Quadrants II and III intersect at intersection 1323. Quadrants III and IV intersect at intersection 1334. Circles 1210b and 1210c generally define the span of the intersections 1312, 1323, 1334 in the vertical −Y' direction. At points on the Mercator projection 1310 where the quadrants I, II, III, IV do not intersect, the circle cross sections 11201a, 1210d, 1210e of smaller diameter are positioned, and the degrees assigned to these sections move in to meet the border of their respective quadrants so that each quadrant only covers 90 degrees over its reduced segment. The Quadrants I, II, III, IV extend vertically to Apical region ending at the common apex 1074 with the apex of each quadrant identified separately, i.e., apex 1074a for Quadrant I, apex 1074b for Quadrant II, apex 1074c for Quadrant III, and apex 1074d for Quadrant IV, although as understood by those skilled in the art, the apexes 1074a, 1074b, 1074c, 1074d intersect to form the common apex 1074. The definitions of the acronyms are as follows:

LAD—left anterior descending (LAD) coronary artery;
LCX—left posterior circumflex (LCX) coronary artery;
RCA—right coronary artery;
PDA—posterior descending artery [Alternatively referred to as inferior descending artery (IDA);
LCA—left coronary artery.

FIG. 24 illustrates a display 1400 that includes a display 1300' of a Mercator projection 1310' of the coronary arteries 1325 on the left ventricle. The display 1300' is identical to display 1300 described above with respect to FIG. 23, except that the axes −X', +X' and −Y' and the cross-sections 1210a, 1210b, 1210c, 1210d, 1210e, have been omitted. The display 1300' is again divided into the four quadrants I (Anteroseptal), II (Anterosuperior), III (Posterolateral) and IV (Inferior). Each quadrant vertical position is identified in descending order as "Basal", "Middle" and "Apical", and the location of a coronary blockage 1335 as a bright red dot. The degree of ischemia that has occurred in ischemic region 1335 may be categorized as small, medium, or large for each of the three conditions and may be shown under a heading Ischemic Area (not shown in FIG. 24). For simplicity, the heading 1412 indicating "3: LAD Large" is shown above the Mercator projection 1310' at the upper left corner. There is a different location for the coronary blockage 1335 for each of nine cases: small, medium and large for LAD (left anterior descending), LCX (left circumflex) and RCA (right coronary artery).

Nine displays for each of these cases can be added. For example, LAD small, medium and large (as illustrated in FIG. 24) spanning quadrant I; LCX small, medium and large spanning quadrants II and III; and RCA small, medium and large spanning quadrant IV, each quadrant extending from the base 1082 to the apexes 1074a, 1074b, 1074c, 1074d.

The display 1300' shows the effects of the location of the coronary blockage 1335. The location of the ST vector, e.g., ST vector 1100 described above with respect to FIGS. 20D, 21 and 22, is located in the vicinity of the centroid 1340.

The centroid 1340 of the ischemic area is the likely location of the vector generated by the ischemia. The location of the blockage 1335 of coronary artery LCA and the effects of this blockage on vessels fed by this artery are shown.

The display 1400 includes a display 1400' of a Mercator projection 1410 that is aligned with the quadrants I, II, II and IV of the Mercator projection 1310'. In the Mercator projection 1310', the location of the coronary blockage (ischemic region 1335) is shown in blue in the Apical region of quadrant I as ischemic region 1335*a* extending to the apex 1074*a* of quadrant I, in quadrant II as ischemic region 1335*b* extending to the apex 1074*b* and ischemic region 1335*c* extending to the apex 1074*c* of quadrants II and III, respectively, and ischemic region 1335*d* extending to the apex 1074*d* of quadrant IV. In the display 1400', the corresponding severity of the coronary blockage (ischemic region 1335) is shown in the corresponding quadrants I (Anteroseptal), II (Anterosuperior), III (Posterolateral) and IV (Inferior).

In corresponding positions below the coronary blockage 1335, in the Mercator projection 1410 of display 1400', the degree or severity of the coronary blockage indicated by ischemic regions 1335*a*, 1335*b*, 1335*c* and 1335*d* is illustrated as ischemia severity indication 1335*a*' in quadrant I (Anteroseptal), ischemia severity indication 1335*b*' in quadrant II (Anterosuperior), ischemia severity indication 1335*c*' in quadrant III (Posterolateral), and ischemia severity indication 1335*d*' in quadrant IV (Inferior), respectively. The degree or severity of the blockage 1335 is illustrated in blue 1345 for a Subendocardial Infarction (partly transmural) and in dark blue 1355 for a Transmural Infarction (completely transmural).

Figure 25:
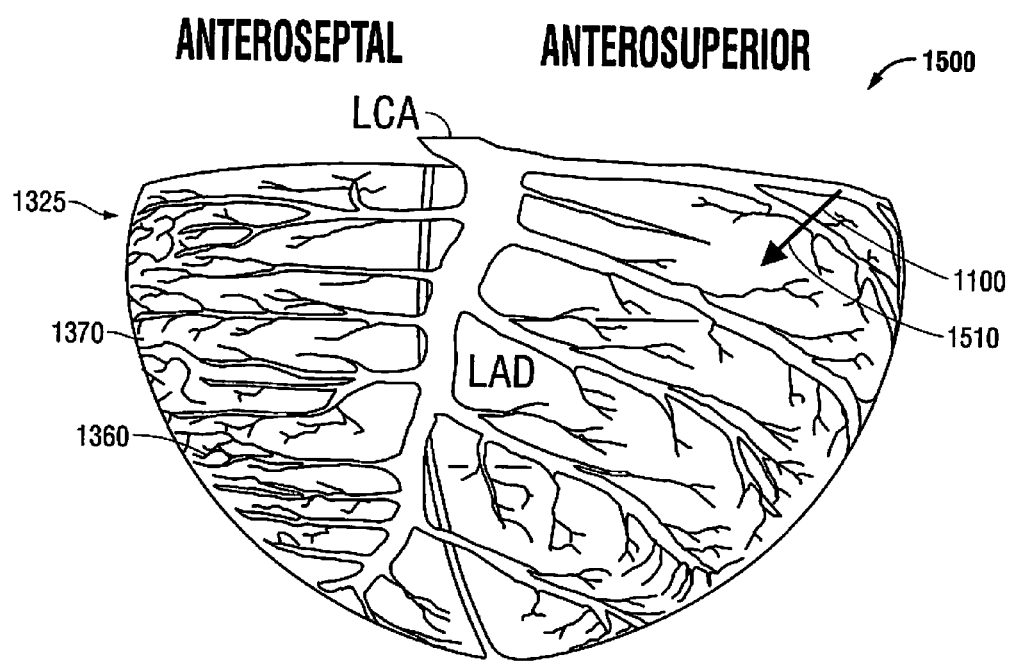
FIG. 25 illustrates one embodiment according to the present disclosure of a 3D rendition of the left ventricle of the heart showing the location of a portion of the left anterior descending (LAD) coronary arteries as seen from a direction that is directly opposite the main LAD section and an ST-vector pointing towards an ischemic region on the surface of the left ventricle.

FIG. 25 illustrates the true location of the coronary arteries 1325 as being on the epicardium 1360 of the Left Ventricle 1370, shown as a 3D rendition in display 1500. Display 1500 illustrates a view when looking at a patient from the left anterior direction. The location of a portion of the LAD coronary arteries 1325 is as would be seen from a direction that is directly opposite the main LAD section. The Mercator projections 1310, 1410 and 1310' of FIGS. 23 and 24, respectively, can be rendered into a 3 dimensional rendition of the LV 1370. The small arrow 1510 at the upper right corner can be located to represent the vector direction of the ST vector 1100.

Those skilled in the art will recognize that, and understand how, the methods and displays of FIG. 20C to FIG. 25 may be applied to locate and display other vectors of interest.

Figure 26:
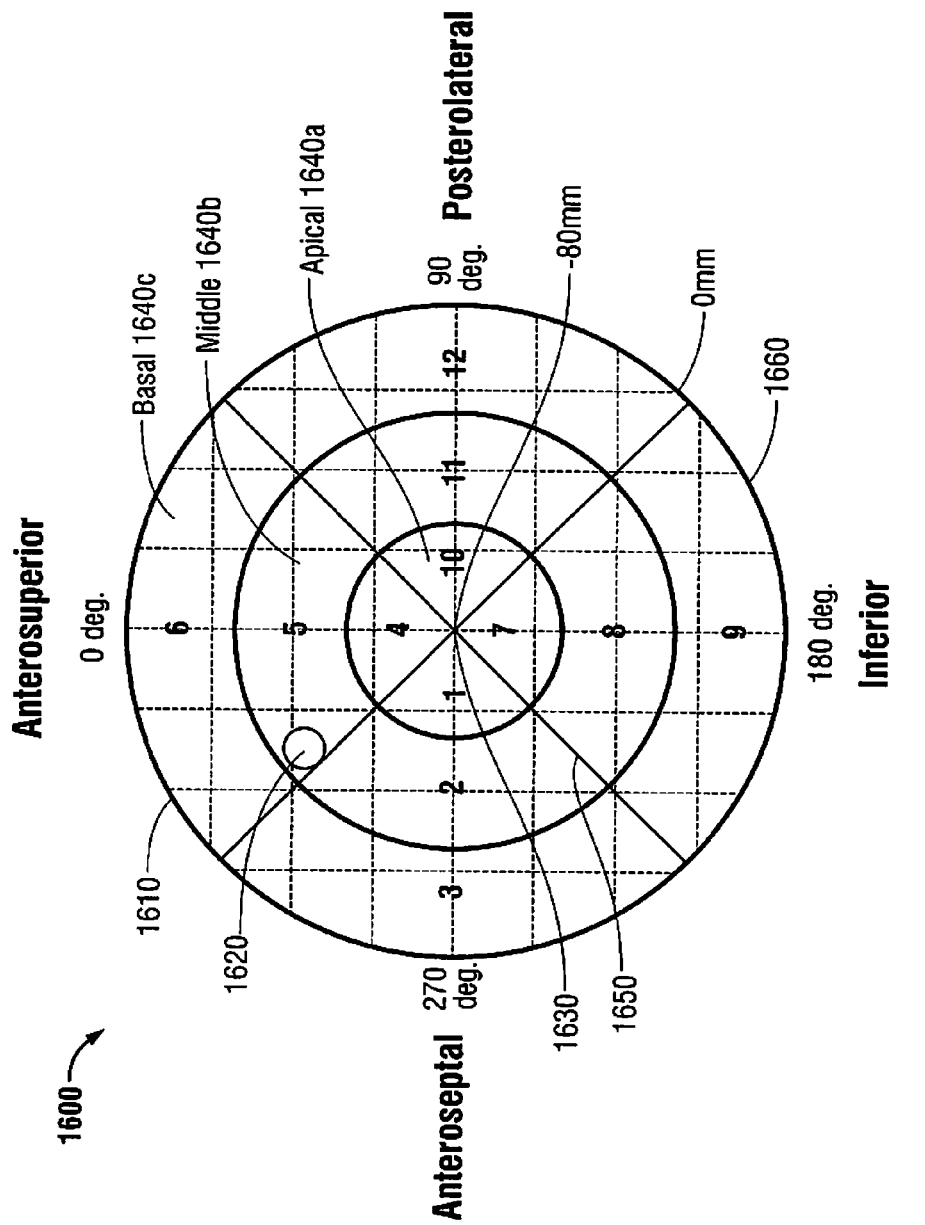
FIG. 26 illustrates one embodiment of a polar plot of the heart that locates a region of ischemia thereon that has been identified via ECG data according to one embodiment of the present disclosure.

FIG. 26 illustrates a display 1600 of a polar plot 1610 of the heart 1070 that is familiar to the medical community and is used in single-photon emission computed tomography (SPECT) imaging to assess the location and extent of the ischemia. The location of the center of the ischemia, shown as a circle 1620, can be displayed on this drawing by showing the azimuth angle in relation to the circles 1640*a*, 1640*b*, 1640*c*, representing the Basal, Middle and Apical regions, respectively, and the radius from the center 1630 as the distance along the vertical axis of the left ventricle. The 0 degree point for measuring the azimuth angle is in the middle of the Anterosuperior quadrant. The radii 1650 extend from −80 mm at the center 1630 to 0 mm at the periphery 1660, representing the epicardium. The numbering 1 through 12 represents a coordinate reference system to identify the particular segments of the Basal, Middle and Apical regions of the polar plot 1610 with respect to particular quadrants Anterosuperior, Posterolateral, Inferior, and Anteroseptal.

Those skilled in the art will recognize that, and understand how, the methods and displays of FIG. 20C to FIG. 22 and FIG. 26 may also be applied to locate and display other vectors of interest.

From the foregoing description of FIGS. 20A-26, it can be appreciated that the embodiments of the present disclosure relate to a method for locating an ischemic region in the heart of a subject. The method includes the steps of establishing three dimensional coordinates axes with respect to the torso, e.g., axes X–Y–Z in FIGS. 20C and 20D of the subject as a reference, establishing as a reference a multi-dimensional representation of the heart e.g., displays 1200*a* and 1200*b* in FIGS. 20C and 20D, respectively, defining at least three dimensional coordinate axes of the heart, e.g., coordinate axes X'–Y'–Z' in FIGS. 20C and 20D. The multi-dimensional representation defines at least the base of the heart and a middle section of the heart, e.g., display 1300 defining Basal and Middle sections in FIG. 23.

The method also includes orienting the three dimensional coordinate axes of the heart, e.g., coordinate axes X'–Y'–Z' in FIGS. 20C and 20D, from an initial position, e.g., at elevation angle 1078 and azimuth angle 1076 in FIG. 20C, offset with respect to the three dimensional coordinates with respect to the torso of the subject, e.g. coordinate axes X–Y–Z in FIG. 20C, to an imaginary position wherein at least one axis of the heart, e.g., axis 1072 in FIG. 20C, is parallel to or coincident with at least one of the three dimensional coordinate axes with respect to the torso of the subject, e.g. the Y' axis being coincident with the Y axis in FIG. 21.

Prior to the step of orienting the three dimensional coordinate axes of the heart from an initial position offset with respect to the three dimensional coordinates with respect to the torso of the subject to an imaginary position wherein at least one axis of the heart is parallel to or coincident with at least one of the three dimensional coordinate axes with respect to the torso of the subject, the method includes performing the steps of: processing data from an electrocardiogram (ECG) with respect to measurements of the signals of at least three leads of the ECG, e.g., limb leads aVL, I, -aVR, II, aVF, III in FIG. 20A or precordial leads V1, V2, V3, V4, V5, V6 in FIG. 20B. Each lead signals a measurement of a magnitude and a direction of an electrical vector, e.g., ST vector 1100 in FIG. 20D associated with the heart 1070 of the subject.

The method may include establishing the electrical center of the heart as the origin of the three dimensional coordinates axes with respect to the torso of the subject, e.g., electrical center 1080 of the heart 1070 as the origin of the XYZ axes in FIG. 20C, and establishing at least one horizontal axis of the three dimensional coordinate axes of the heart in the initial offset position to extend along the base of the heart, e.g., horizontal axis X' or Z' extending along the base 1082 of heart 1070 in FIG. 20C. The method also includes establishing at least one of the three dimensional coordinate axes of the heart in the initial offset position to pass through the electrical center of the heart, e.g., vertical axis Y' through electrical center 1080 of the heart 1070 in FIG. 20C.

The method may include transforming the data from the ECG with respect to the measurements of the at least three leads of the ECG, e.g., limb leads aVL, I, -aVR, II, aVF, III in FIG. 20A or precordial leads V1, V2, V3, V4, V5, V6 in FIG. 20B, to substantially coincide with the three dimensional coordinate axes of the heart in the initial offset position, e.g., the X'Y'Z' coordinate axes in FIG. 20C, and rotating with respect to at least one of the three dimensional coordinate axes with respect to the torso, e.g., one of the coordinate axes XYZ of FIG. 20C, the at least one of the three dimensional coordinate axes of the heart passing through the electrical center of the heart, e.g. coordinate axis Y' in FIG. 20C passing through the electrical center 1080 of the heart 1070.

The step of rotating may be performed by rotating a vertical axis of the at least one of the three dimensional coordinate axes of the heart passing through the electrical center of the heart, e.g., coordinate axis Y' in FIG. 20C passing through the electrical center 1080 with respect to a plane defined by at least two of the three dimensional coordinate axes with respect to the torso, e.g., the XZ plane defined by the X and Z coordinate axes in FIG. 20D. The step of rotating a vertical axis thereby changes an elevation angle of the vertical axis of the at least one of the three dimensional coordinate axes of the heart passing through the electrical center of the heart, e.g., changing elevation angle of the Y' axis of the heart 1070 passing through the electrical center 1080, with respect to the plane defined by the at least two of the three dimensional coordinate axes with respect to the torso, e.g., the XZ plane defined by the X and Z coordinate axes in FIG. 20D.

The step of rotating may also additionally include rotating a horizontal axis of the at least one of the three dimensional coordinate axes of the heart extending along the base of the heart with respect to a horizontal axis of the at least one of the three dimensional coordinate axes with respect to the torso, e.g., rotating coordinate axis X' with respect to axis X in FIG. 20C. The step of rotating a horizontal axis thereby changes an azimuth angle of the horizontal axis of the at least one of the three dimensional coordinate axes of the heart extending along the base of the heart with respect to the horizontal axis of the at least one of the three dimensional coordinate axes with respect to the torso, e.g. changing azimuth angle 1076 of the horizontal axis X in FIG. 20C.

The steps of rotating a vertical axis and of rotating a horizontal axis thereby effects the step of orienting the three dimensional coordinate axes of the heart, e.g., coordinate axes X'–Y'–Z' in FIGS. 20C and 20D, from an initial position, e.g., at elevation angle 1078 and azimuth angle 1076 in FIG. 20C, offset with respect to the three dimensional coordinates with respect to the torso of the subject, e.g., coordinate axes XYZ in FIG. 20C, to an imaginary position wherein at least one axis of the heart, e.g., axis 1072 in FIG. 20C, is parallel to or coincident with at least one of the three dimensional coordinate axes with respect to the torso, e.g. the Y' axis being coincident with the Y axis in FIG. 21.

The step of changing the elevation angle may change the elevation angle from a first elevation angle, e.g., elevation angle 1078 in FIG. 20C, having a magnitude greater than zero to a second elevation angle, e.g., elevation angle 1242 in FIG. 21, having a magnitude of substantially 0 degrees or substantially 90 degrees.

The step of changing the azimuth angle may change the azimuth angle from a first azimuth angle, e.g., azimuth angle 1076 in FIG. 20C, having a magnitude greater than zero to a second azimuth angle, e.g., azimuth angle 1240 in FIG. 21, having a magnitude of substantially 0 degrees or substantially 90 degrees.

The method may further include the steps of: establishing the electrical center of the heart, e.g., electrical center 1080 of the heart 1070 in FIG. 20D, as the origin of the electrical vector, e.g., the ST vector 1100 in FIG. 20D. The origin of the electrical vector, e.g., ST vector 1100, thereby coincides with the origin of the three dimensional coordinates axes with respect to the torso of the subject, e.g., coordinate axes XYZ in FIG. 20D. The magnitude and the direction of the electrical vector in a first position of the electrical vector, e.g., ST vector 1100 in FIG. 20D, is referenced with respect to the three dimensional coordinates axes with respect to the torso of the subject, e.g., coordinate axes XYZ in FIG. 20D.

The magnitude and the direction of the electrical vector in the first position, e.g., ST vector 1100 in FIG. 20D, defines a first elevation angle, e.g., elevation angle 1104 in FIG. 20D, with respect to a plane defined by the three dimensional coordinates axes with respect to the torso of the subject, e.g. with respect to the XZ plane in FIG. 20D.

Similarly, the magnitude and the direction of the electrical vector in the first position, e.g., ST vector 1100 in FIG. 20D, defines a first azimuth angle, e.g., azimuth angle 1102 in FIG. 20D, with respect to an axis of the three dimensional coordinates axes with respect to the torso of the subject, e.g. with respect to the X axis in FIG. 20D.

The method may include rotating the electrical vector from the first position to a position defining a second elevation angle, e.g., elevation angle 1242 in FIG. 21, being referenced with respect to a plane defined by the three dimensional coordinates axes with respect to the heart in the imaginary position, e.g., plane XZ defined by the XYZ coordinate axes in FIG. 21, wherein at least one axis of the heart is parallel to or coincident with at least one of the three dimensional coordinate axes with respect to the torso, e.g. the Y' axis of the heart being coincident with the Y axis of the torso.

The method may include rotating the electrical vector from the first position to a position defining a second azimuth angle, e.g., azimuth angle 1240 in FIG. 21, being referenced with respect to an axis defined by the three dimensional coordinates axes with respect to the heart in the imaginary position, e.g., axis X' in FIG. 21, that is parallel to or coincident with at least one of the three dimensional coordinate axes with respect to the torso, e.g., coordinate axes XYZ in FIG. 21.

The step of establishing as a reference a multi-dimensional representation of the heart may be performed by establishing the reference multi-dimensional representation of the heart such that the origin of the three dimensional coordinate axes of the heart substantially coincides with the base of the heart, e.g., display 1200a in FIG. 21 or display 1200b in FIG. 22 may be established as reference multi-dimensional representations of the heart such that the coordinate axes X'Y'Z' substantially coincide with the base 1082 of the heart 1070.

Additionally, the step of establishing as a reference a multi-dimensional representation of the heart may be performed by establishing the reference multi-dimensional representation of the heart such that the origin of the three dimensional coordinate axes of the torso substantially coincides with the electrical center of the heart, e.g., display 1200a in FIG. 21 or display 1200b in FIG. 22 may be established as reference multi-dimensional representations of the heart such that the origin of the coordinate axes XYZ substantially coincides with the electrical center 1080 of the heart 1070.

The method may include the step of transforming the ECG data identifying the electrical vector, e.g., ST vector 1100, to correlate with the second elevation angle, e.g. elevation angle 1242, of the electrical vector and with the second azimuth angle, e.g., azimuth angle 1240, of the electrical vector. The method step of transforming the ECG data identifying the electrical vector may include calculating the elevation of the electrical vector, e.g. ST vector 1100, with respect to the second elevation angle, e.g. elevation angle 1242.

The step of establishing as a reference a multi-dimensional representation of the heart defining at least three dimensional coordinate axes of the heart may thereby prescribe a surface of the heart on the reference multi-dimensional representation of the heart, e.g., the display 1200b in FIG. 22 being a multi-dimensional representation of the heart prescribes a surface of the heart, e.g., the epicardium 1075, on the display 1200b.

The method may further include the step of identifying on the reference multi-dimensional representation of the heart the elevation of the intersection of the electrical vector with the surface of the heart, e.g. points of intersection 1105, 1115, 1125, 1135, 1145, 1155 of vectors 1100, 1110, 1120, 1130, 1140, 1150, respectively, with the surface 1075 of the heart 1070, e.g., with the epicardium, in FIG. 22. The step of identifying on the reference multi-dimensional representation of the heart the elevation of the intersection of the electrical vector with the surface of the heart, e.g. points of intersection 1105, 1115, 1125, 1135, 1145, 1155 of vectors 1100, 1110, 1120, 1130, 1140, 1150, respectively, with the surface 1075 of the heart 1070, e.g., with the epicardium 1075, in FIG. 22 may include calculating the elevation of the electrical vector, e.g, ST vector 1100, with respect to the elevation of the electrical vector, e.g., ST vector 1100, with respect to the second elevation angle, e.g., elevation angle 1242. transforming the ECG data identifying the electrical vector, e.g., ST vector 1100, to correlate with the elevation of the electrical vector, e.g., ST vector 1100, with respect to the second elevation angle, e.g., elevation angle 1242.

The method may further include the step of identifying on the reference multi-dimensional representation of the heart, e.g., on display 1300, the azimuth of the intersection, e.g., points of intersection 1105, 1115, 1125, 1135, 1145, 1155 in FIG. 22, of the electrical vector, e.g., vectors 1100, 1110, 1120, 1130, 1140, 1150, respectively, with the surface 1075 of the heart 1070. The step of identifying on the reference multi-dimensional representation of the heart, e.g., on display 1300, the azimuth of the intersection, e.g., points of intersection 1105, 1115, 1125, 1135, 1145, 1155 in FIG. 22, of the electrical vector, e.g., vectors 1100, 1110, 1120, 1130, 1140, 1150, respectively, with the surface 1075 of the heart 1070 may include transforming the ECG data identifying the electrical vector, e.g., ST vector 1100, to correlate with the second azimuth angle, e.g. azimuth angle 1240, of the electrical vector, e.g., vectors 1100, 1110, 1120, 1130, 1140, 1150, respectively, with the surface 1075 of the heart 1070.

The method may further include the step of locating the center of an ischemic region based on the identifying of the elevation and azimuth of the electrical vector with respect to the reference multi-dimensional representation of the heart, e.g. locating centroid 1340 as the center of the ischemic region based on the identifying of the elevation and azimuth of the electrical vector, e.g., ST vector 1100, with respect to the Mercator projections 1310' and 1410 in FIG. 24.

The method may also include displaying the electrical vector on a medical display for analyzing heart signals to illustrate the center of the ischemic region, e.g., displaying the centroid 1340 as the ST vector 1100, with respect to the Mercator projections 1310' and 1410 in FIG. 24.

Those skilled in the art will recognize that, and understand how, the method for locating an ischemic region in the heart of a subject may be employed to construct various medical displays for locating and displaying an ischemic region in the heart of a subject, as illustrated by displays 1000a, 1000b, 1000c, 1000d in FIGS. 20A-20D, respectively, by displays 1200a and 1200b in FIGS. 21 and 22, respectively, displays 1300 and 1400 in FIGS. 23 and 24, respectively, and displays 1500 and 1600 in FIGS. 25 and 26, respectively.

For example, the present disclosure discloses a medical display for locating an ischemic region in the heart of a subject, e.g., displays 1300 and 1400 in FIGS. 23 and 24, respectively. The display portrays the location of the ischemic region, e.g., ischemic region 1340 in FIG. 24, via three dimensional coordinates axes established with respect to the torso as a reference, e.g., coordinate axes XYZ in FIGS. 20C and 20D, via a multi-dimensional representation of the heart established as a reference defining at least three dimensional coordinate axes of the heart, e.g., displays 1300 and 1400 in FIGS. 23 and 24 or displays 1200a and 1200b in FIGS. 21 and 22, respectively, the multi-dimensional representation defining at least the base of the heart and a middle section of the heart, e.g. base 1082 of the heart 1070 and the Basal and Middle sections defined in display 1300 of FIG. 23; and the three dimensional coordinate axes of the heart, e.g., coordinate axes X'-Y'-Z' in FIGS. 20C-20D, being oriented from an initial position, e.g., at elevation angle 1078 and azimuth angle 1076 in FIG. 20C, offset with respect to the three dimensional coordinates with respect to the torso of the subject, e.g., coordinate axes X-Y-Z in FIG. 20C, to an imaginary position wherein at least one axis of the heart, e.g. axis 1072 in FIG. 20C, is parallel to or coincident with at least one of the three dimensional coordinate axes with respect to the torso of the subject, e.g., the Y' axis being coincident with the Y axis in FIG. 21.

While the above description contains many specifics, these specifics should not be construed as limitations in the scope of the present disclosure, but merely as exemplifications of particular embodiments thereof. Those skilled in the art will envision many other possible variations that are within the scope and spirit of the present disclosure.

What is claimed is:

1. A method for locating an ischemic region in the heart of a subject, the method comprising the steps of:
    establishing three dimensional coordinates axes with respect to the torso of the subject as a reference;
    establishing as a reference a multi-dimensional representation of the heart defining at least three dimensional coordinate axes of the heart, the multi-dimensional representation defining at least the base of the heart and a middle section of the heart;
    processing data from an electrocardiogram (ECG) with respect to measurements of the signals of at least three leads of the ECG, each lead signaling a measurement of a magnitude and a direction of an electrical vector associated with the heart of the subject;
    establishing the electrical center of the heart as the origin of the three dimensional coordinates axes with respect to the torso of the subject;
    establishing at least one horizontal axis of the three dimensional coordinate axes of the heart in the initial offset position to extend along the base of the heart;
    establishing at least one of the three dimensional coordinate axes of the heart in the initial offset position to pass through the electrical center of the heart;
    transforming the data from the ECG with respect to the measurements of the at least three leads of the ECG to substantially coincide with the three dimensional coordinate axes of the heart in the initial offset position; and
    rotating, with respect to at least one of the three dimensional coordinate axes with respect to the torso, the at least one of the three dimensional coordinate axes of the heart passing through the electrical center of the heart; and
    orienting the three dimensional coordinate axes of the heart from an initial position offset with respect to the three dimensional coordinates with respect to the torso of the subject to an imaginary position wherein at least one axis of the heart is parallel to or coincident with at least one of the three dimensional coordinate axes with respect to the torso of the subject.

2. The method according to claim 1, wherein the step of rotating, with respect to at least one of the three dimensional coordinate axes with respect to the torso, the at least one of the three dimensional coordinate axes of the heart passing through the electrical center of the heart is performed by rotating a vertical axis of the at least one of the three dimensional coordinate axes of the heart passing through the electrical center of the heart with respect to a plane defined by at least two of the three dimensional coordinate axes with respect to the torso, thereby changing an elevation angle of the vertical axis of the at least one of the three dimensional coordinate axes of the heart passing through the electrical center of the heart with respect to the plane defined by the at least two of the three dimensional coordinate axes with respect to the torso.

3. The method according to claim 2, further comprising the step of: rotating a horizontal axis of the at least one of the three dimensional coordinate axes of the heart extending along the base of the heart with respect to a horizontal axis of the at least one of the three dimensional coordinate axes with respect to the torso, thereby changing an azimuth angle of the horizontal axis of the at least one of the three dimensional coordinate axes of the heart passing through the electrical center of the heart with respect to the horizontal axis of the at least one of the three dimensional coordinate axes with respect to the torso, effecting thereby the step of orienting the three dimensional coordinate axes of the heart from an initial position offset with respect to the three dimensional coordinates with respect to the torso of the subject to an imaginary position wherein at least one axis of the heart is parallel to or coincident with at least one of the three dimensional coordinate axes with respect to the torso.

4. The method according to claim 3, wherein the changing of the elevation angle changes the elevation angle from a first elevation angle having a magnitude greater than zero to a second elevation angle having a magnitude of one of substantially 0 degrees and substantially 90 degrees.

5. The method according to claim 4, wherein the changing of the azimuth angle changes the azimuth angle from a first azimuth angle having a magnitude greater than zero to a second azimuth angle having a magnitude of one of substantially 0 degrees and substantially 90 degrees.

6. The method according to claim 3, further comprising the steps of:
establishing the electrical center of the heart as the origin of the electrical vector, the origin of the electrical vector coinciding thereby with the origin of the three dimensional coordinates axes with respect to the torso of the subject, the magnitude and the direction of the electrical vector in a first position of the electrical vector being referenced with respect to the three dimensional coordinates axes with respect to the torso of the subject, the magnitude and the direction of the electrical vector in the first position defining a first elevation angle with respect to a plane defined by the three dimensional coordinates axes with respect to the torso of the subject, the magnitude and the direction of the electrical vector in the first position defining a first azimuth angle with respect to an axis of the three dimensional coordinates axes with respect to the torso of the subject; and rotating the electrical vector from the first position to a position defining a second elevation angle being referenced with respect to a plane defined by the three dimensional coordinates axes with respect to the heart in the imaginary position wherein at least one axis of the heart is parallel to or coincident with at least one of the three dimensional coordinate axes with respect to the torso.

7. The method according to claim 6, further comprising the step of:
rotating the electrical vector from the first position to a position defining a second azimuth angle being referenced with respect to an axis defined by the three dimensional coordinates axes with respect to the heart in the imaginary position wherein at least one axis of the heart is parallel to or coincident with at least one of the three dimensional coordinate axes with respect to the torso.

8. The method according to claim 7, wherein the step of establishing as a reference a multi-dimensional representation of the heart is performed by establishing the reference multi-dimensional representation of the heart such that the origin of the three dimensional coordinate axes of the heart substantially coincides with the base of the heart.

9. The method according to claim 8, wherein the step of:
establishing as a reference a multi-dimensional representation of the heart is performed by establishing the reference multi-dimensional representation of the heart such that the origin of the three dimensional coordinate axes of the torso substantially coincides with the electrical center of the heart.

10. The method according to claim 9, further comprising the step of:
transforming the ECG data identifying the electrical vector to correlate with the second elevation angle of the electrical vector and with the second azimuth angle of the electrical vector.

11. The method according to claim 10, wherein the step of transforming the ECG data includes:
calculating the elevation of the electrical vector with respect to the second elevation angle.

12. The method according to claim 10, wherein the step of establishing as a reference a multi-dimensional representation of the heart defining at least three dimensional coordinate axes of the heart thereby prescribes a surface of the heart on the reference multi-dimensional representation of the heart, the method further comprising the step of:
identifying on the reference multi-dimensional representation of the heart the elevation of the intersection of the electrical vector with the surface of the heart.

13. The method according to claim 12, wherein the step of identifying on the reference multi-dimensional representation of the heart the elevation of the intersection of the electrical vector with the surface of the heart includes calculating the elevation of the electrical vector with respect to the second elevation angle.

14. The method according to claim 12, further comprising the step of:
identifying on the reference multi-dimensional representation of the heart the azimuth of the intersection of the electrical vector with the surface of the heart.

15. The method according to claim 14, wherein the step of identifying on the reference multi-dimensional representation of the heart the azimuth of the intersection of the electrical vector with the surface of the heart includes calculating the azimuth of the electrical vector with respect to the second azimuth angle.

16. The method according to claim 14, further comprising the step of:
locating the center of an ischemic region based on the identifying of the elevation and azimuth of the electrical vector with respect to the reference multi-dimensional representation of the heart.

17. The method according to claim 16, further comprising the step of:
displaying the electrical vector on a medical display for analyzing heart signals to illustrate the center of the ischemic region.

* * * * *